United States Patent
Yano et al.

(10) Patent No.: US 8,206,806 B2
(45) Date of Patent: *Jun. 26, 2012

(54) CYANINE COMPOUND AND OPTICAL RECORDING MATERIAL

(75) Inventors: Toru Yano, Tokyo (JP); Satoshi Yanagisawa, Tokyo (JP); Yohei Aoyama, Tokyo (JP); Koichi Shigeno, Tokyo (JP)

(73) Assignee: Adeka Corporation, Tokyo (JP)

( * ) Notice: Subject to any disclaimer, the term of this patent is extended or adjusted under 35 U.S.C. 154(b) by 917 days.

This patent is subject to a terminal disclaimer.

(21) Appl. No.: 12/295,449

(22) PCT Filed: Mar. 23, 2007

(86) PCT No.: PCT/JP2007/055998
§ 371 (c)(1),
(2), (4) Date: Sep. 30, 2008

(87) PCT Pub. No.: WO2007/114073
PCT Pub. Date: Oct. 11, 2007

(65) Prior Publication Data
US 2009/0054652 A1   Feb. 26, 2009

(30) Foreign Application Priority Data

Mar. 31, 2006   (JP) .................... 2006-096534

(51) Int. Cl.
*B32B 3/02* (2006.01)
*G11B 7/24* (2006.01)

(52) U.S. Cl. .......... 428/64.8; 428/64.4; 430/270.2; 430/270.21; G9B/7.151; 548/427; 548/455; 548/468; 548/490

(58) Field of Classification Search ............ 428/64.4, 428/64.8; 430/270.2, 270.21; G9B/7.151; 548/427, 455, 468, 490
See application file for complete search history.

(56) References Cited

U.S. PATENT DOCUMENTS

| | | | |
|---|---|---|---|
| 6,482,494 B2 | 11/2002 | Je et al. | |
| 7,247,417 B2 | 7/2007 | Fukuzawa et al. | |
| 2009/0234122 A1* | 9/2009 | Aizawa et al. | 546/6 |
| 2010/0003445 A1* | 1/2010 | Yano et al. | 428/64.4 |

FOREIGN PATENT DOCUMENTS

| | | |
|---|---|---|
| JP | 52-90307 | 7/1977 |
| JP | 62-207685 | 9/1987 |
| JP | 05173282 A * | 7/1993 |
| JP | 2001-342365 | 12/2001 |
| JP | 2002-293844 | 10/2002 |
| JP | 2003-231359 | 8/2003 |
| JP | 2004-98542 | 4/2004 |
| JP | 2005-59601 | 3/2005 |
| JP | 2005-297407 | 10/2005 |
| WO | 01/44374 | 6/2001 |
| WO | 2006/011306 | 2/2006 |
| WO | 2006/038464 | 4/2006 |
| WO | 2006/123786 | 11/2006 |

OTHER PUBLICATIONS

Machine translation of JP05-173282 acquired on Aug. 29, 2011.*
Communication pursuant to Article 94(3) EPC in European Counterpart Application No. 07739439.3 issued on Sep. 1, 2011.
Extended European Search Report in European Counterpart Application No. 11004603.4 issued on Sep. 5, 2011.
Notification of the First Office Action in Chinese Application No. 200780011412.3 issued on Aug. 3, 2011 with English Translation.

* cited by examiner

*Primary Examiner* — Gerard Higgins
(74) *Attorney, Agent, or Firm* — Young & Thompson

(57) ABSTRACT

A cyanine compound is represented by formula (I):

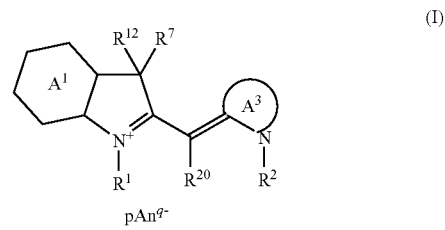

$A^1$: benzene or naphthalene ring. $A^3$: 5- or 6-membered ring. $R^1$, $R^2$: hydrogen atom and the like. $R^7$: an alkyl group and the like. $R^{12}$: a substituent by formula (II) or (II'). $R^{20}$: a hydrogen atom and the like. $An^{q-}$: a q-valent anion. q: 1 or 2; p: a coefficient for neutral charge. In formula (II): bond between L and T is a double, conjugated double, or triple bond. L: carbon atom. T: carbon, oxygen, sulfur, or nitrogen atom. x, y, z: 0 or 1. s: 0-4. $R^{13}$: hydrogen atom and the like. $R^{14}$, $R^{15}$, and $R^{16}$: hydrogen atom and the like. In formula (II'), the bond between L' and T' is a double or conjugated double bond. L': carbon atom. T':

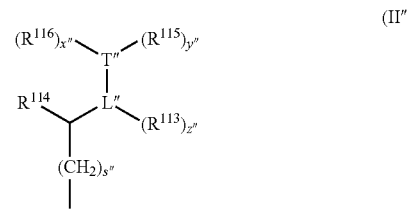

carbon, oxygen, nitrogen atom. s': 0-4. Ring containing L' and T': 5-membered ring, may contain a heteroatom.

13 Claims, No Drawings

CYANINE COMPOUND AND OPTICAL RECORDING MATERIAL

TECHNICAL FIELD

The present invention relates to a novel cyanine compound and an optical recording material comprising the cyanine compound. The cyanine compound is useful as an optical recording agent to be comprised in an optical recording material, which is used in an optical recording layer of an optical element and the like, especially an optical recording medium, information being recorded thereon and reproduced therefrom as information patterns by means of a laser and the like. The optical recording material is especially useful for an optical recording medium, which is capable of high-density optical recording and reproduction by a laser and the like, the laser having emissions in ultraviolet and visible regions, and being of low energy.

BACKGROUND ART

The optical recording media are in widespread use, generally due to its superior characteristics such as large recording capacities, and noncontact recording or reproduction. In the write-once optical discs such as WORM, CD-R, DVD±R, and the like, recording is carried out by focusing the laser light on a minute area of the recording layer to change properties of the optical recording layer, while reproduction is performed based on a difference in intensities of light reflected from the recorded area and non-recorded area.

Presently, in the optical discs mentioned above, the wavelength of a semiconductor laser used for recording and reproduction is between 750 and 830 nm for CD-R and between 620 and 690 nm for DVD-R. However, in order to realize further increase in capacity, an optical disc which uses short-wavelength laser light is being explored. For example, one which uses light of wavelength between 380 and 420 nm as the recording light is under study.

In an optical recording medium for the short-wavelength recording light, various compounds are used to form the optical recording layer. For example, reported are in Patent Document 1 a hemicyanine dye, in Patent Document 2 a trimethine compound, in Patent Document 3 a porphyrin compound, and in Patent Document 4 a monomethine cyanine dye which has a specific structure. However, as an optical recording material used to form an optical recording layer, these compounds have problems that their absorption wavelength characteristics are not necessarily suitable or that they do not have excellent recording characteristics.

Patent Document 1: Japanese Patent Laid-Open Publication No. 2001-342365
Patent Document 2: Japanese Patent Laid-Open Publication No. 2004-98542
Patent Document 3: Japanese Patent Laid-Open Publication No. 2005-59601
Patent Document 4: International Publication No. WO/01/044374

DISCLOSURE OF THE INVENTION

Problems to be Solved by the Invention

Accordingly, an object of the present invention is to provide a novel compound having optical properties suitable for forming an optical recording layer of an optical recording medium for short-wavelength recording light and to provide an optical recording material comprising the compound.

Means for Solving the Problems

The present inventors conducted diligent research and, as a result, found a cyanine compound of a specific molecular structure, having absorption wavelength characteristics suitable for forming an optical recording layer of an optical recording medium for short-wavelength recording light. The inventors envisaged that the use of this compound may solve the problems.

The present invention has been made based on the above findings and accomplished the objects by providing a cyanine compound represented by the following general formula (I).

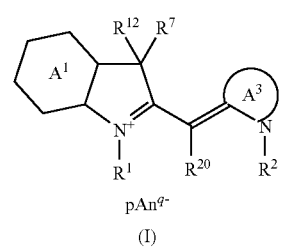

[Formula 1]

(I)

wherein, the ring $A^1$ represents benzene or naphthalene ring; the ring $A^3$ represents 5-membered or 6-membered ring, where the 5-membered or 6-membered ring may be condensed with other rings or may be substituted; $R^1$ and $R^2$ each independently represent a hydrogen atom, an alkyl group having 1 to 8 carbon atoms, an aryl group having 6 to 20 carbon atoms, an arylalkyl group having 7 to 20 carbon atoms, a substituent represented by the following general formula (II), (II'), or (III); $R^7$ represents an alkyl group having 1 to 8 carbon atoms, an aryl group having 6 to 20 carbon atoms, an arylalkyl group having 7 to 20 carbon atoms, or a substituent represented by the general formula (II) or (II'); $R^2$ represents a substituent represented by the following general formula (II) or (II'); $R^{20}$ represents a hydrogen atom, a hydroxyl group, a halogen atom, a nitro group, a cyano group, an alkyl group having 1 to 8 carbon atoms, an aryl group having 6 to 20 carbon atoms, an arylalkyl group having 7 to 20 carbon atoms, a heterocyclic group having 2 to 20 carbon atoms, or an amino group; the methylene group of the alkyl group having 1 to 8 carbon atoms may be replaced by —O—, —S—, —CO—, —COO—, —SO$_2$—, —NH—, —CONH—, —N═CH—, —C≡C—, or —CH═CH—; $An^{q-}$ represents q-valent anion; q represents 1 or 2; p represents a coefficient to keep the charge neutral:

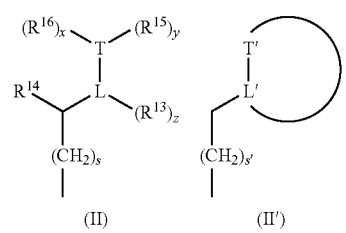

[Formula 2]

(II)    (II')

in the general formula (II), the bond between L and T is a double, conjugated double, or triple bond; L represents a carbon atom; T represents a carbon, oxygen, sulfur, or nitrogen atom; x, y, and z represent 0 or 1; s represents a number from 0 to 4; $R^{13}$ represents a hydrogen atom, a halogen atom, an alkyl group having 1 to 4 carbon atoms which may be substituted with a halogen atom, or an alkoxy group having 1 to 4 carbon atoms which may be substituted with a halogen atom; $R^{14}$, $R^{15}$, and $R^{16}$ each independently represent a hydrogen atom, a halogen atom, an alkyl group having 1 to 4 carbon atoms which may be substituted with a halogen atom, or an aryl group having 6 to 12 carbon atoms, where $R^{14}$ and $R^{16}$ may be linked to form a ring structure; in the general formula (II'), the bond between L' and T' is a double or conjugated double bond; L' represents a carbon atom; T' represents a carbon, oxygen, or nitrogen atom; s' represents a number from 0 to 4; the ring containing L' and T' represents a 5-membered or 6-membered ring which may contain a hetero atom, or a naphthalene, quinoline, isoquinoline, anthracene, or anthraquinone ring; the rings containing L' and T' may be substituted with a halogen atom, or a nitro, cyano, alkyl, or alkoxy group:

[Formula 3]

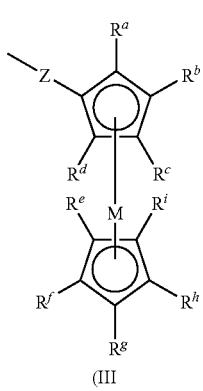

(III)

wherein, $R^a$ to $R^i$ each independently represent a hydrogen atom, a hydroxy group, or an alkyl group having 1 to 4 carbon atoms, where the methylene group of the alkyl group may be replaced by —O— or —CO—; Z represents a direct bond or an alkylene group having 1 to 8 carbon atoms which may be substituted; the methylene group of the alkylene group may be replaced by —O—, —S—, —CO—, —COO—, —OCO—, —SO$_2$—, —NH—, —CONH—, —NHCO—, —N═CH—, or —CH═CH—; M represents a metal atom.

In addition, the present invention has accomplished the objects by providing a cyanine compound represented by the following general formula (VI).

[Formula 4]

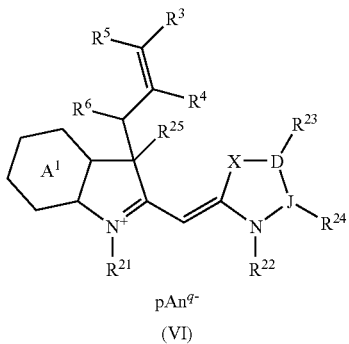

(VI)

wherein the ring $A^1$ represents benzene or naphthalene ring; X represents an oxygen, sulfur, or selenium atom, —$CR^8R^9$—, —NH—, or —NR'—; R', $R^{21}$, and $R^{22}$ each independently represent a hydrogen atom, an alkyl group having 1 to 8 carbon atoms, an aryl group having 6 to 20 carbon atoms, an arylalkyl group having 7 to 20 carbon atoms, or a substituent represented by the following general formula (VII); $R^3$, $R^4$, $R^5$, and $R^6$ each independently represent a hydrogen atom, a halogen atom, an alkyl group having 1 to 8 carbon atoms, or an aryl group having 6 to 12 carbon atoms; $R^3$ and $R^4$ may be linked to form a ring; $R^{25}$ and the groups belonging to X, namely $R^8$ and $R^9$, each independently represent an alkyl group having 1 to 8 carbon atoms, an aryl group having 6 to 20 carbon atoms, an arylalkyl group having 7 to 20 carbon atoms, or a substituent represented by the following general formula (VII); $R^8$ and $R^9$ may be linked to form a ring; $R^{23}$ and $R^{24}$ each independently represent a hydrogen atom, a hydroxyl group, an alkyl group having 1 to 8 carbon atoms, an alkoxy group having 1 to 8 carbon atoms, an aryl group having 6 to 30 carbon atoms, a halogen atom, a nitro group, a cyano group, or a substituent represented by the general formula (III); $R^{23}$ and $R^{24}$ may be linked to form a ring structure; the methylene group of the alkyl group having 1 to 8 carbon atoms may be replaced by —O— or —CH═CH—; $An^{q-}$ represents a q-valent anion; q represents 1 or 2; p represents a coefficient to keep the charge neutral; D and J are the same as in the general formula (V):

[Formula 5]

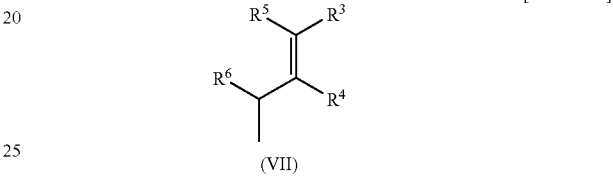

(VII)

wherein $R^3$, $R^4$, $R^5$, and $R^6$ are the same as in the general formula (VI).

Further, the present invention has accomplished the objects by providing an optical recording material comprising at least one kind of the cyanine compounds.

Furthermore, the present invention has accomplished the objects by providing an optical recording medium comprising an optical recording layer formed by the optical recording material on a substrate.

BEST MODE FOR CARRYING OUT THE INVENTION

Hereafter, the cyanine compound represented by the general formulae (I) and (VI), and the optical recording material containing the compound will be described in detail based on preferred embodiments.

First, the cyanine compound represented by the general formula (I) will be described.

In the cyanine compound of the present invention, the alkyl group in the general formula (I), having 1 to 8 carbon atoms and represented by $R^1$, $R^2$, $R^7$, and $R^{20}$, includes methyl, ethyl, propyl, isopropyl, butyl, sec-butyl, tert-butyl, isobutyl, amyl, isoamyl, tert-amyl, hexyl, cyclohexyl, cyclohexylmethyl, cyclohexylethyl, heptyl, isoheptyl, tert-heptyl, n-octyl, isooctyl, tert-octyl, 2-ethylhexyl, and the like; the aryl group having 6 to 20 carbon atoms, represented by $R^1$, $R^2$, $R^7$, and $R^{20}$, includes phenyl, naphthyl, anthracene-1-yl, phenanthrene-1-yl, and the like; the arylalkyl group having 7 to 20 carbon atoms, represented by $R^1$, $R^2$, $R^7$, and $R^{20}$, includes benzyl, phenethyl, 2-phenylpropane, diphenylmethyl, triphenylmethyl, styryl, cinnamyl, and the like; the halogen atom represented by $R^{20}$ includes fluorine, chlorine, bromine, and iodine; the heterocyclic group having 2 to 20 carbon atoms, represented by $R^{20}$, includes pyridyl, pyrimidyl, pyridazyl, piperazyl, piperidyl, pyranyl, pyrazolyl, triazyl, pyrrolidyl, quinolyl, isoquinolyl, imidazolyl, benzimidazolyl, triazolyl, furyl, furanyl, benzofuranyl, thienyl, thiophenyl, benzothiophenyl, thiadiazolyl, thiazolyl, benzothiazolyl, oxazolyl, benzoxazolyl, isothiazolyl, isoxazolyl, indolyl, urolidyl, morpholinyl, thiamorpholinyl, 2-pyrrolidinone-1-yl, 2-piperidone-1-yl, 2,4-dioxyimidazolidine-3-yl, 2,4-dioxyoxazolidine-3-yl, and the like; the amino group represented by $R^{20}$ include amino, ethylamino, dimethylamino, diethylamino, butylamino, cyclopentylamino, 2-ethylhexylamino, dodecylamino, anilino, chlorophenylamino, toluidino, anicidino, N-methylanilino, diphenylamino, naphthylamino, 2-pyridylamino, methoxycarbonylamino, phenoxycarbonylamino, acetylamino, benzoylamino, formylamino, pivaloylamino, lauroylamino, carbamoyl amino, N,N-dimethylaminocarbonylamino, N,N-diethylaminocarbonylamino, morpholinocarbonylamino, methoxycarbonylamino, ethoxycarbonylamino, t-butoxycarbonylamino, n-octadecyloxycarbonylamino, N-methylmethoxycarbonylamino, phenoxycarbonylamino, sulfamoylamino, N,N-dimethylaminosulfonylamino, methylsulfonylamino, butylsulfonylamino, phenylsulfonylamino, trimethylammonio, triethylammonio, and the like, where the amino group having a quaternary nitrogen may form a salt with an anion.

In the general formula (I), the benzene or naphthalene ring represented by the ring $A^1$ may be condensed with other rings or may be substituted; the 5-membered ring represented by the ring $A^3$ includes pyrrole, pyrolidine, pyrazole, imidazole, imidazolidine, oxazole, isoxazole, isoxazolidine, thiazole, isothiazolidine rings, and the like; the 6-membered ring represented by the ring $A^3$ includes piperidine, piperazine, morpholine, thiomorpholine, pyridine, pyrazine, pyrimidine, pyridazine, triazine rings, and the like. These rings may be condensed with other rings or may be substituted, with examples including quinoline, isoquinoline, indole, urolidine, benzoxazole, benzotriazole rings, and the like.

In the general formula (II), the halogen atom represented by $R^{13}$, $R^{14}$, $R^{15}$, and $R^{16}$ includes fluorine, chlorine, bromine, iodine, and the like; the alkyl group having 1 to 4 carbon atoms in the general formula (I), represented by $R^{13}$, $R^{14}$, $R^{15}$, and $R^{16}$, includes methyl, ethyl, propyl, isopropyl, butyl, sec-butyl, tert-butyl, isobutyl, and the like; a group resulting from replacement of a methylene group of the alkyl group by —O— includes methoxy, ethoxy, propyloxy, isopropyloxy, methoxymethyl, ethoxymethyl, 2-methoxyethyl, and the like; a group resulting from replacement of methylene group of the alkyl groups by —CO— includes acetyl, 1-carbonylethyl, acetylmethyl, 1-carbonylpropyl, 2-oxobutyl, 2-acetylethyl, 1-carbonylisopropyl, and the like.

The alkoxy group having 1 to 4 carbon atoms, represented by $R^{13}$, includes methyloxy, chloromethyloxy, trifluoromethyloxy, cyanomethyloxy, ethyloxy, dichloroethyloxy, propyloxy, isopropyloxy, butyloxy, sec-butyloxy, tert-butyloxy, isobutyloxy, and the like; the aryl groups having 6 to 12 carbon atoms, represented by $R^{14}$, $R^{15}$, and $R^{16}$, includes, among the groups exemplified in the description of the general formula (I), those which satisfy the specified range of number of carbon atoms.

The ring structure formed by linking of $R^{14}$ and $R^{16}$ includes cyclopropane, cyclobutane, cyclopentane, cyclohexane, tetrahydropyran, piperidine, piperazine, pyrrolidine, morpholin, thiomorpholin, pyridine, pyrazine, pyrimidine, pyridazine, triazine, quinoline, isoquinoline, imidazole, oxazole, imidazolidine, pyrazolidine, isoxazolidine, isothiazolidine rings, and the like, where these rings may be condensed with other rings or may be substituted.

In the general formula (II'), the 5-membered ring which may contain an heteroatom includes cyclopentene, cyclopentadiene, imidazole, thiazole, pyrrazole, oxazole, isoxazole, thiophene, furan, pyrrole rings, and the like; the 6-membered ring which may contain a heteroatom includes benzene, pyridine, piperazine, piperidine, morpholin, pyrazine, pyrone, pyrrolidine rings, and the like; these rings may be condensed with other rings or may be substituted.

In the general formula (III), the alkyl group having 1 to 4 carbon atoms, represented by $R^a$ to $R^i$, includes methyl, ethyl, propyl, isopropyl, butyl, sec-butyl, tert-butyl, isobutyl, and the like; a group resulting from replacement of a methylene group of the alkyl group with —O— include methoxy, ethoxy, propyloxy, isopropyloxy, methoxymethyl, ethoxymethyl, 2-methoxyethyl, and the like; a group resulting from replacement of methylene groups of the alkyl group with —CO— includes acetyl, 1-carbonylethyl, acetylmethyl, 1-carbonylpropyl, 2-oxobutyl, 2-acetylethyl, 1-carbonylisopropyl, and the like; the alkylene group having 1 to 8 carbon atoms, represented by Z which may be substituted includes methylene, ethylene, propylene, methylethylene, butylene, 1-methylpropylene, 2-methylpropylene, 1,2-dimethylpropylene, 1,3-dimethylpropylene, 1-methylbutylene, 2-methylbutylene, 3-methylbutylene, 4-methylbutylene, 2,4-dimethylbutylene, 1,3-dimethylbutylene, pentylene, hexylene, heptylene, octylene, ethane-1,1-diyl, propane-2,2-diyl, and the like; a group resulting from replacement of methylene groups of the alkylene group with —O—, —S—, —CO—, —COO—, —OCO—, —SO$_2$—, —NH—, —CONH—, —NHCO—, —N=CH—, or —CH=CH—, includes methyleneoxy, ethyleneoxy, oxymethylene, thiomethylene, carbonylmethylene, carbonyloxymethylene, methylenecarbonyloxy, sulfonylmethylene, aminomethylene, acetylamino, ethylene carboxyamide, ethane imide-yl, ethenylene, propenylene, and the like; the metal atom represented by M includes Fe, Co, Ni, Ti, Cu, Zn, Zr, Cr, Mo, Os, Mn, Ru, Sn, Pd, Rh, Pt, Ir, and the like.

In the general formula (I), the anion represented by An$^{q-}$ includes, as monovalent anion, for example, halide ion such as chloride, bromide, iodide, fluoride ion, and the like; inorganic anion such as perchlorate, chlorate, thiocyanate, hexafluorophosphate, hexafluoroantimonate, tetrafluoroborate ion, and the like; organic sulfonate ion such as benzenesulfonate, toluenesulfonate, trifluoromethanesulfonate, diphenylamine-4-sulfonate, 2-amino-4-methyl-5-chlorobenzenesulfonate, and 2-amino-5-nitrobenzenesulfonate ion, and sulfonate ion described in Japanese Patent Laid-Open Publication No. H8-253705, Japanese Patent Application Laid-Open No. 2004-503379, Japanese Patent Laid-Open Publication No. 2005-336150, International Publication No. WO/2006/28006, and the like; organic phosphate-related ion such as octyl phosphate, dodecyl phosphate, octadecyl phosphate, phenyl phosphate, nonylphenyl phosphate, 2,2'-methylenebis(4,6-di-tert-butylphenyl) phosphonate ion, and the like; bistrifluoromethylsulfonylimide and bisperfluorobutanesulfonylimide anions; perfluoro-4-ethylcyclohexanesulfonate ion; tetrakis(pentafluorophenyl)borate ion; tetrakis(pentafluorophenyl)gallate ion; tris(fluoroalkylsulfonyl)carbanion; dibenzoyl tartrate ion, and the like. As divalent anion, for example, benzenedisulfonate ion, naphthalenedisulfonate ion, and the like may be cited. There may also be used, according to necessity, a quencher anion that can deactivate (quench) the active molecules in the exited state and anions of metallocene compounds such as ferrocene, ruthenocene, and the like, which have an anionizable group such as carboxylic acid, phosphonic acid, and sulfonic acid groups on the cyclopentadienyl group, and the like.

The quencher anion includes, for example, those represented by the following general formulae (A) and (B), or chemical formulae (C) and (D), or anions described in Japanese Patent Laid-Open Publication No. S60-234892, H5-43814, H5-305770, U6-239028, H9-309886, H9-323478, 1110-45767, H11-208118, 2000-168237, 2002-201373, 2002-206061, and 2005-297407; Japanese Patent Application Publication No. H7-96334; International Publication Nos. WO/98/29257 and WO/2006/123786, and the like.

[Formula 6]

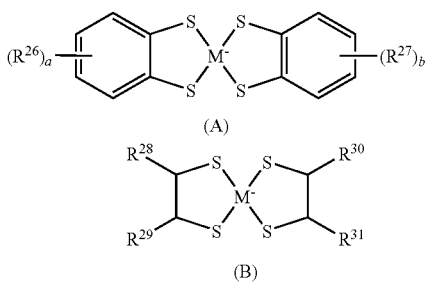

(A)

(B)

wherein M represents a nickel, cobalt, or copper atom; $R^{26}$ and $R^{27}$ each independently represent a halogen atom, an alkyl group having 1 to 8 carbon atoms, an aryl group having 6 to 30 carbon atoms, or a —$SO_2$-G group, G representing an alkyl, aryl that may be substituted with a halogen atom, dialkylamino, diarylamino, piperidino, or morpholino groups; a and b each independently represent a number from 0 to 4; further, $R^{28}$, $R^{29}$, $R^{30}$, and $R^{31}$ each independently represent an alkyl, alkylphenyl, alkoxyphenyl, or halogenated phenyl groups.

[Formula 7]

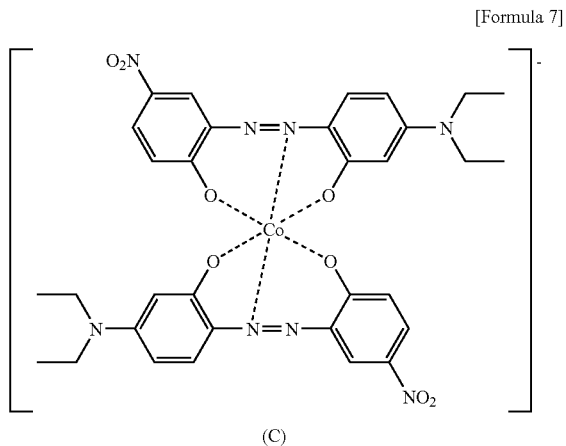

(C)

[Formula 8]

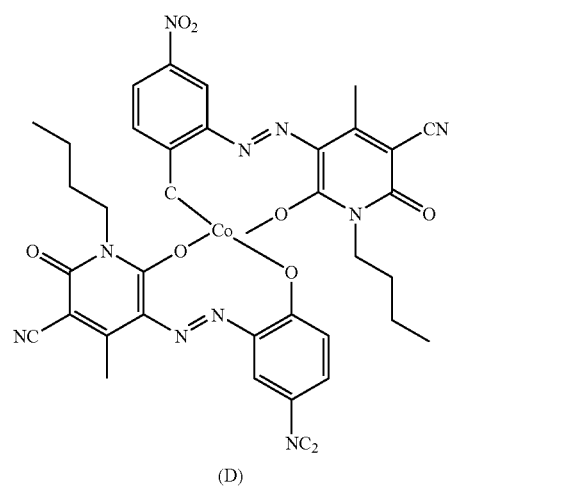

(D)

Among the cyanine compounds represented by the general formula (I) of the present invention, the followings are preferable because their production costs are low and their absorption wavelength characteristics between 380 to 420 nm are especially suited for formation of an optical recording layer of an optical recording medium for a short-wavelength laser. The preferable compounds include those represented by the following general formulae (IV) and (V); those having a naphthalene ring as the ring $A^1$; those having as $R^1$ and/or $R^2$ a substituent represented by the general formula (II); and those having as $An^{q-}$ a q-valent anion without an azo bond.

[Formula 9]

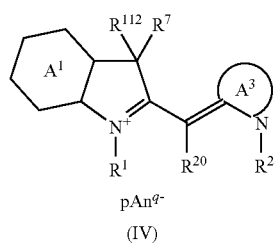

(IV)

wherein $R^{112}$ represents a substituent represented by the following general formula (II''); the rings $A^1$ and $A^3$, $R^1$, $R^2$, $R^7$ $R^{20}$, $An^{q-}$, q, and p are the same as in the general formula (I):

[Formula 10]

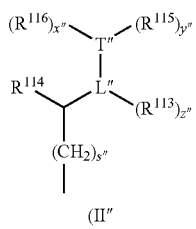

(II'')

wherein the bond between L'' and T'' is a double or triple bond; L'' represents a carbon atom; T'' represents a carbon, oxygen, sulfur, or nitrogen atom; x'', y'', and z'' represent 0 or 1; s'' represents a number from 0 to 4; $R^{113}$ represents a hydrogen atom, a halogen atom, an alkyl group having 1 to 4 carbon atoms which may be substituted with a halogen atom, or an alkoxy group having 1 to 4 carbon atoms which may be substituted with a halogen atom; $R^{114}$, $R^{115}$, and $R^{116}$ each independently represent a hydrogen atom, a halogen atom, an alkyl group having 1 to 4 carbon atoms which may be substituted with a halogen atom, or an aryl group having 6 to 12 carbon atoms.

[Formula 11]

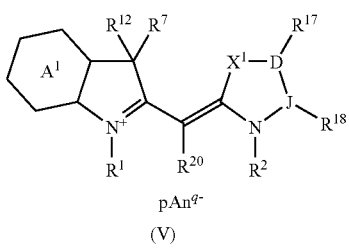

(V)

wherein $X^1$ is an oxygen, sulfur, or selenium atom, —NH—, or —NR—; the bond between D and J is a single, double, or conjugated double bond; D and J are carbon atoms; $R^{17}$, $R^{18}$, and R each independently represent a hydrogen atom, an alkyl group having 1 to 8 carbon atoms, an aryl group having 6 to 20 carbon atoms, an arylalkyl group having 7 to 20 carbon atoms, a substituent represented by the general formula (II) or (II'); the ring $A^1$, $R^1$, $R^2$, $R^7$, $R^{12}$, $R^{20}$, $An^{q-}$, q and p are the same as in the general formula (I).

In the general formula (II''), the halogen atom and the alkyl group having 1 to 4 carbon atoms, represented by $R^{113}$, $R^{114}$, $R^{115}$, and $R^{116}$, include those exemplified in the description of the general formula (II); the alkoxy group having 1 to 4 carbon atoms, represented by $R^{113}$, includes those exemplified in the description of the general formula (II); the aryl group having 6 to 12 carbon atoms, represented by $R^{114}$, $R^{115}$, and $R^{116}$, includes those exemplified in the description of the general formula (II).

Further, in the general formula (V), the alkyl group having 1 to 8 carbon atoms, aryl group having 6 to 20 carbon atoms, and arylalkyl group having 7 to 20 carbon atoms, each represented by $R^{17}$, $R^{18}$, and a group belonging to $X^1$, namely R, include those groups exemplified in the description of the general formula (I).

Each of the following groups may have a substituent: the alkyl group having 1 to 8 carbon atoms, represented by $R^1$, $R^2$, $R^7$, $R^{17}$, $R^{18}$, $R^{20}$, and R; the aryl group having 6 to 20 carbon atoms, represented by $R^1$, $R^2$, $R^7$, $R^{17}$, $R^{18}$, $R^{20}$, and R; the arylalkyl group having 7 to 20 carbon atoms, represented by $R^1$, $R^2$, $R^7$, $R^{17}$, $R^{18}$, $R^{20}$, and R; the heterocyclic group having 2 to 20 carbon atoms, represented by $R^{20}$; and benzene or naphthalene ring represented by the ring $A^1$. The substituent includes the following. In addition, when $R^1$, $R^2$, $R^7$, $R^{17}$, $R^{18}$, $R^{20}$, and R represent a group containing carbon atoms such as an alkyl group having 1 to 8 carbon atoms and the like, and when, at the same time, those groups possess a substituent having carbon atoms among the following substituents, the total number of carbon atoms of $R^1$, $R^2$, $R^7$, $R^{17}$, $R^{18}$, $R^{20}$, and R, respectively and that of the substituent is supposed to satisfy the specified range.

The above-mentioned substituent includes an alkyl group such as methyl, ethyl, propyl, isopropyl, cyclopropyl, butyl, sec-butyl, tert-butyl, isobutyl, amyl, isoamyl, tert-amyl, cyclopentyl, hexyl, 2-hexyl, 3-hexyl, cyclohexyl, bicyclohexyl, 1-methylcyclohexyl, heptyl, 2-heptyl, 3-heptyl, isoheptyl, tert-heptyl, n-octyl, isooctyl, tert-octyl, 2-ethyl hexyl, nonyl, isononyl, decyl, and the like; an alkoxy group such as methyloxy, ethyloxy, propyloxy, isopropyloxy, butyloxy, sec-butyloxy, tert-butyloxy, isobutyloxy, amyloxy, isoamyloxy, tert-amyloxy, hexyloxy, cyclohexyloxy, heptyloxy, isoheptyloxy, tert-heptyloxy, n-octyloxy, isooctyloxy, tert-octyloxy, 2-ethylhexyloxy, nonyloxy, decyloxy, and the like; an alkylthio group such as methylthio, ethylthio, propylthio, isopropylthio, butylthio, sec-butylthio, tert-butylthio, isobutylthio, amylthio, isoamylthio, tert-amylthio, hexylthio, cyclohexylthio, heptylthio, isoheptylthio, tert-heptylthio, n-octylthio, isooctylthio, tert-octylthio, 2-ethylhexylthio, and the like; an alkenyl group such as vinyl, 1-methylethenyl, 2-methylethenyl, 2-propenyl, 1-methyl-3-propenyl, 3-butenyl, 1-methyl-3-butenyl, isobutenyl, 3-pentenyl, 4-hexenyl, cyclohexenyl, bicyclohexenyl, heptenyl, octenyl, decenyl, pentadecnyl, eicocenyl, tricocenyl, and the like; an arylalkyl group such as benzyl, phenethyl, diphenylmethyl, triphenylmethyl, styryl, cinnamyl, and the like; an aryl group such as phenyl, naphthyl, and the like; an aryloxy group such as phenoxy, naphthyloxy, and the like; an arylthio group such as phenylthio, naphthylthio, and the like; a heterocyclic group such as pyridyl, pyrimidyl, pyridazyl, piperidyl, pyranyl, pyrazolyl, triazyl, pyrrolyl, quinolyl, isoquinolyl, imidazolyl, benzimidazolyl, triazolyl, furyl, furanyl, benofuranyl, thienyl, thiophenyl, benzothiophenyl, thiadiazolyl, thiazolyl, benzothiazolyl, oxazolyl, benzoxazolyl, isothiazolyl, isoxazolyl, indolyl, 2-pyrrolidinone-1-yl, 2-piperidone-1-yl, 2,4-dioxyimidazolidine-3-yl, 2,4-dioxyoxazolidine-3-yl, and the like; a halogen atom such as fluorine, chlorine, bromine, iodine, and the like; an acyl group such as acetyl, 2-chloroacetyl, propionyl, octanoyl, acryloyl, methacryloyl, phenylcarbonyl (benzoyl), phthaloyl, 4-trifluoromethylbenzoyl, pivaloyl, saliciloyl, oxaloyl, stearoyl, methoxycarbonyl, ethoxycarbonyl, t-butoxycarbonyl, n-octadecyloxycarbonyl, carbamoyl, and the like; an acyloxy group such as acetyloxy, benzoyloxy, and the like; a substituted amino group such as amino, ethylmino, dimethylamino, diethylamino, butylamino, cyclopentylamino, 2-ethylhexylamino, dodecylamino, anilino, chlorophenylamino, toluidino, anicidino, N-methylanilino, diphenylamino, naphthylamino, 2-pyridylamino, methoxycarbonylamino, phenoxycarbonylamino, acetylamino, benzoylamino, formylamino, pivaloylamino, lauroylamino, carbamoylamino, N,N-dimethylaminocarbonylamino, N,N-diethylaminocarbonylamino, morpholinocarbonylamino, methoxycarbonylamino, ethoxycarbonylamino, t-butoxycarbonylamino, n-octadecyloxycarbonylamino, N-methylmethoxycarbonylamino, phenoxycarbonylamino, sulfamoylamino, N,N-dimethylaminosulfonylamino, methylsulfonylamino, butylsulfonylamino, phenylsulfonylamino, and the like; a sulfonamide, sulfonyl, carboxyl, cyano, sulfo, hydroxy, nitro, mercapto, imide, carbamoyl, sulfonamide groups and the like. These groups may be further substituted. In addition, the carboxyl and sulfo groups may be in the form of salts.

Secondly, the cyanine compound represented by the general formula (VI) will be described.

In the general formula (VI), the alkyl group having 1 to 8 carbon atoms, represented by $R^3$, $R^4$, $R^5$, $R^6$, $R^{21}$, $R^{22}$, $R^{23}$, $R^{24}$ and $R^{25}$, and the groups belonging to X, namely $R^8$, $R^9$, and R', includes those exemplified in the description of the general formula (I); an aryl group having 6 to 20 carbon atoms, represented by $R^{21}$, $R^{22}$ and $R^{25}$, and groups belonging to X, namely $R^8$, $R^9$ and R', includes those exemplified in the description of the general formula (I); an arylalkyl group having 7 to 20 carbon atoms, represented by $R^{21}$, $R^{22}$, and $R^{25}$, and groups belonging to X, namely $R^8$, $R^9$, and R', includes those exemplified in the description of the general formula (I).

Further, a halogen atom represented by $R^3$, $R^4$, $R^5$, $R^6$, $R^{23}$, and $R^{24}$ includes those exemplified in the description of the general formula (I); an aryl group having 6 to 12 carbon atoms, represented by $R^3$, $R^4$, $R^5$, and $R^6$, includes those exemplified in the description of the general formula (II).

An alkoxy group having 1 to 8 carbon atoms, represented by $R^{23}$ and $R^{24}$, includes methyloxy, ethyloxy, propyloxy, isopropyloxy, butyloxy, sec-butyloxy, tert-butyloxy, isobutyloxy, amyloxy, isoamyloxy, tert-amyloxy, hexyloxy, cyclohexyloxy, heptyloxy, isoheptyloxy, tert-heptyloxy, n-octyloxy, isooctyloxy, tert-octyloxy, 2-ethylhexyloxy, and the like.

An aryl group having 6 to 30 carbon atoms, represented by $R^{23}$ and $R^{24}$, includes tetracenyl, pentacenyl, crycenyl, triphenylenyl, pyrenyl, picenyl, perilenyl, and the like, in addition to those exemplified in the description of the general formula (I).

In the general formula (VI), the ring structure formed by linking of $R^3$ and $R^4$, of $R^{23}$ and $R^{24}$, and of groups belonging to X, namely $R^8$ and $R^9$, includes those exemplified as the ring structure formed by linking of $R^{14}$ and $R^{16}$ in the general formula (II).

Each of the following groups may have a substituent: the alkyl group having 1 to 8 carbon atoms, represented by $R^3$, $R^4$, $R^5$, $R^6$, $R^{21}$, $R^{22}$, $R^{23}$, $R^{24}$, and $R^{25}$, and the groups belonging to X, namely $R^8$, $R^9$, and R'; the aryl group having 6 to 20 carbon atoms, represented by $R^{21}$, $R^{22}$, and $R^{25}$, and the group belonging to X, namely $R^8$, $R^9$, and R'; the arylalkyl groups having 7 to 20 carbon atoms, represented by $R^{21}$, $R^{22}$, and $R^{25}$, and groups belonging to X, namely $R^8$, $R^9$, and R; the heterocyclic group having 2 to 20 carbon atoms represented by $R^{19}$; and the benzene or naphthalene ring represented by the ring $A^2$. The substituent includes those exemplified in the description of the general formula (I) In addition, when $R^3$, $R^4$, $R^5$, $R^6$, $R^{21}$, $R^{22}$, $R^{23}$, $R^{24}$, and $R^{25}$, and the groups belonging to X, namely $R^8$, $R^9$, and R', represent a group containing carbon atoms such as an alkyl group having 1 to 8 carbon atoms and the like, and when, at the same time, those groups possess a substituent having carbon atoms among the above-mentioned substituents, the total number of carbon atoms of $R^3$, $R^4$, $R^5$, $R^6$, $R^{21}$, $R^{22}$, $R^{23}$, $R^{24}$, and $R^{25}$, and the groups belonging to X, namely $R^8$, $R^9$, and R', respectively, and that of the substituent, is supposed to satisfy the specified range.

Among the cyanine compounds represented by the general formula (VI), those represented by the following general formula (VIII) or (IX) are preferable because their production costs are low and their absorption wavelength characteristics between 380 and 420 nm are especially suited for formation of an optical recording layer of an optical recording medium for a short-wavelength laser.

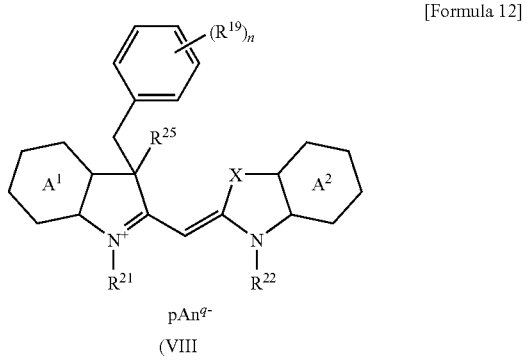

[Formula 12]

(VIII)

wherein $A^2$ represents benzene or naphthalene ring; $R^{19}$ represents a hydrogen atom, a hydroxyl group, an alkyl group having 1 to 8 carbon atoms, an alkoxy group having 1 to 8 carbon atoms, an aryl group having 6 to 30 carbon atoms, a heterocyclic group having 2 to 20 carbon atoms, a halogen atom, a nitro group, or a cyano group; n is a number from 1 to 5; $A^1$, $R^{21}$, $R^{22}$, $R^{25}$, X, $An^{q-}$, p, and q are the same as in the general formula (VI).

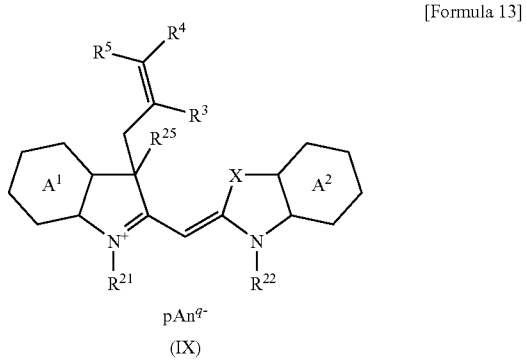

[Formula 13]

(IX)

wherein $A^1$, $R^3$, $R^4$, $R^5$, $R^{21}$, $R^{22}$, $R^{25}$, X, $An^{q-}$, p, and q are the same as in the general formula (VI); $A^2$ is the same as in the general formula (VIII).

In the general formula (VIII), the heterocyclic group having 2 to 20 carbon atoms, represented by $R^{19}$, includes pyridyl, pyrimidyl, pyridazyl, piperazyl, piperidyl, pyranyl, pyrazolyl, triazyl, pyrrolidyl, quinolyl, isoquinolyl, imidazolyl, benzoimidazolyl, triazolyl, furyl, furanyl, benzofuranyl, thienyl, thiophenyl, benzothiophenyl, thiadiazolyl, thiazolyl, benzothiazolyl, oxazolyl, benzoxazolyl, isothiazolyl, isoxazolyl, indolyl, urolidyl, morpholinyl, thiomorpnolinyl, 2-pyrrolidinone-1-yl, 2-piperidone-1-yl, 2,4-dioxyimidazolidine-3-yl, 2,4-dioxyoxazolidine-3-yl, and the like.

Further, the alkyl group having 1 to 8 carbon atoms and halogen atom represented by $R^{19}$ include those exemplified in the description of the general formula (I). The alkoxy group having 1 to 8 carbon atoms and aryl group having 6 to 30 carbon atoms include those exemplified in description of the general formula (VI).

When the cyanine compound of the present invention, represented by the general formula (I) or (VI), is used as an optical recording material which will be described later, they may be used singly or in combination of two or more kinds.

Specific examples of the cyanine compound represented by the general formulae (I) and (VI) include the following compound Nos. 1 to 51. It is noted that the following examples show only indolium cations, omitting anions. In the cyanine compound of the present invention, the polymethine chain may have a resonance structure and the cation may reside on the nitrogen atom of another heterocyclic skeleton.

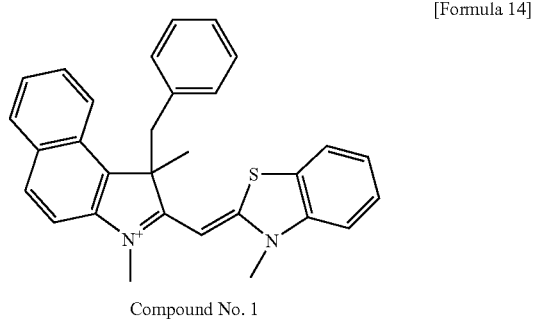

[Formula 14]

Compound No. 1

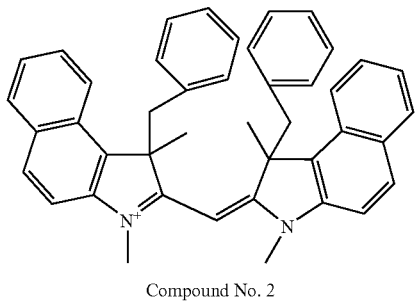

Compound No. 2

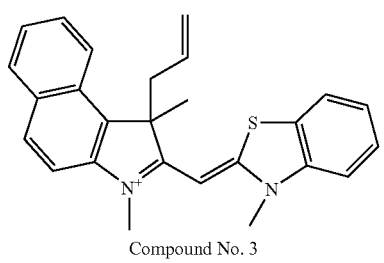

Compound No. 3

[Formula 15]
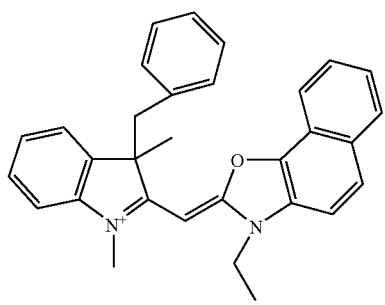
Compound No. 4
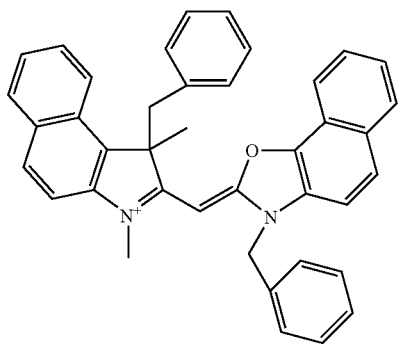
Compound No. 5
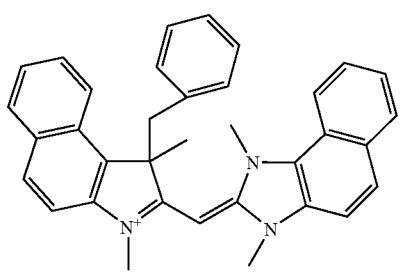
Compound No. 6
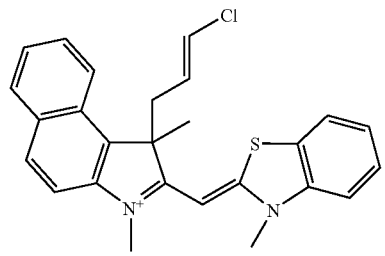
Compound No. 7
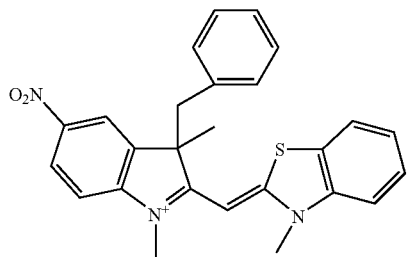
Compound No. 8
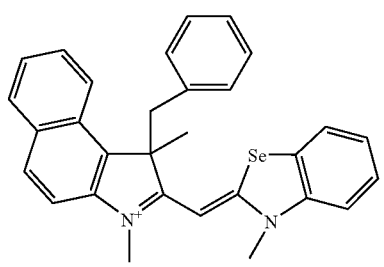
Compound No. 9
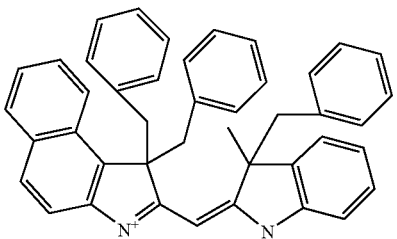
Compound No. 10
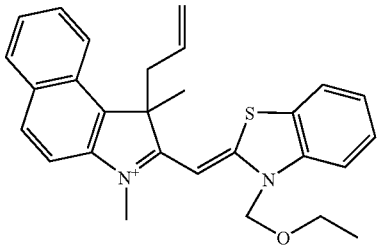
Compound No. 11
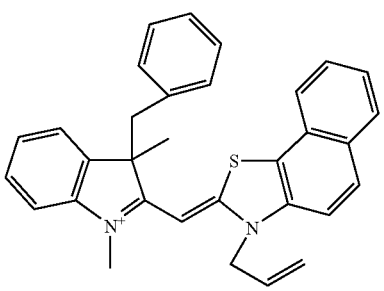
Compound No. 12
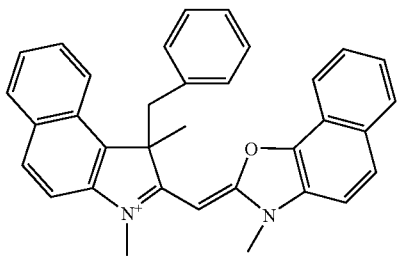
Compound No. 13

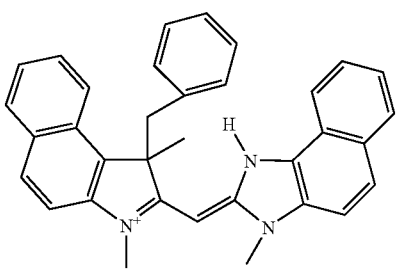
Compound No. 14
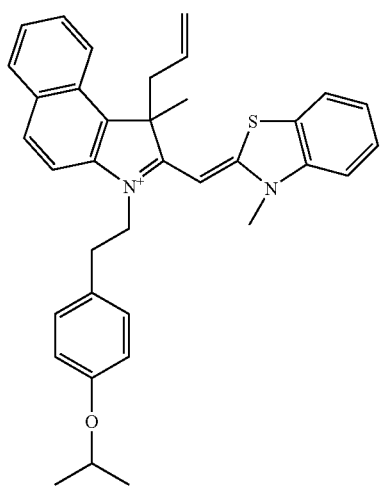
Compound No. 15
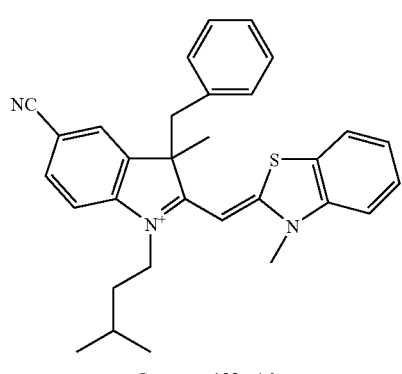
Compound No. 16
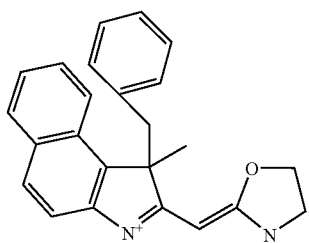
Compound No. 18
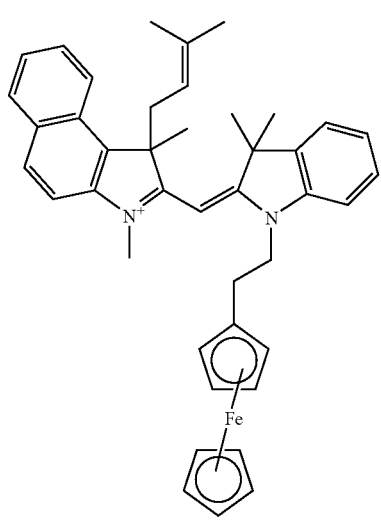
Compound No. 19
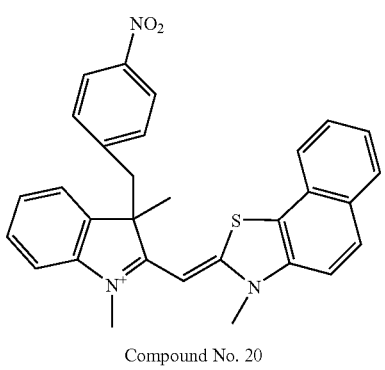
Compound No. 20
[Formula 16]
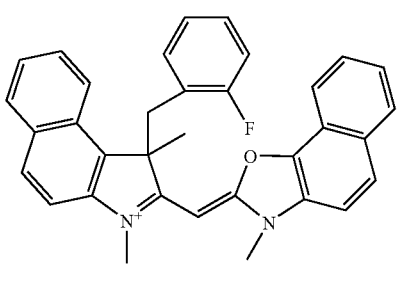
Compound No. 21

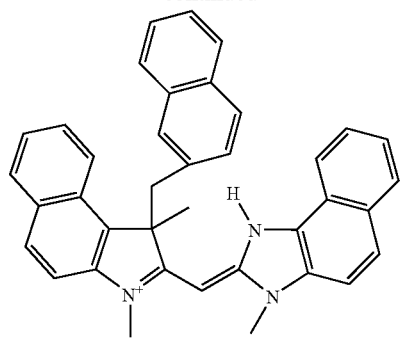
Compound No. 22
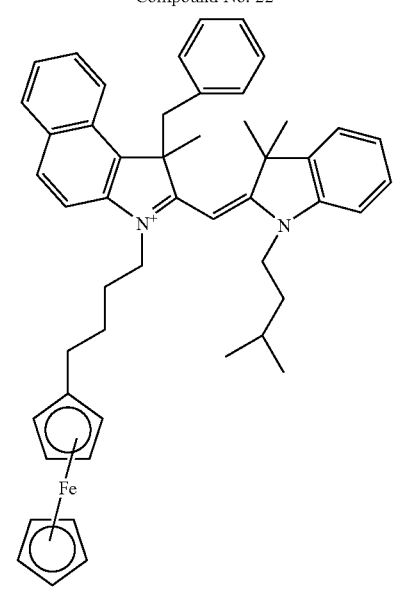
Compound No. 23
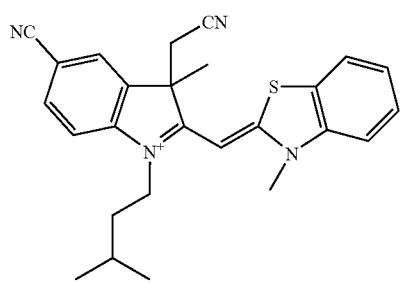
Compound No. 24
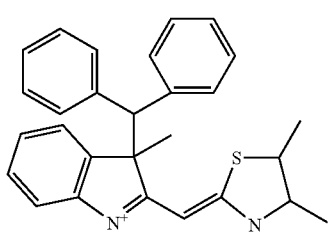
Compound No. 25
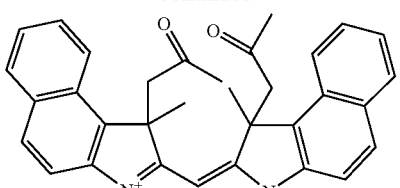
Compound No. 26
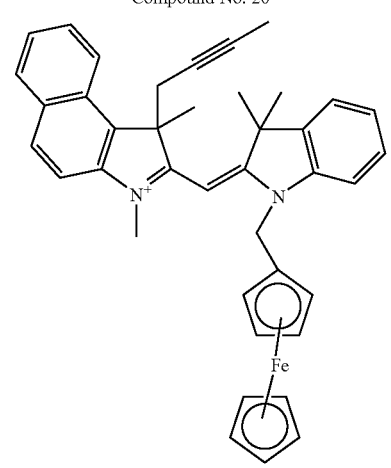
Compound No. 27
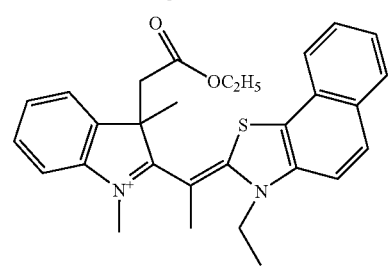
Compound No. 28
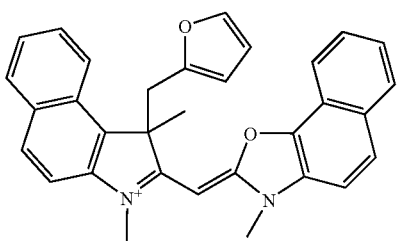
Compound No. 29
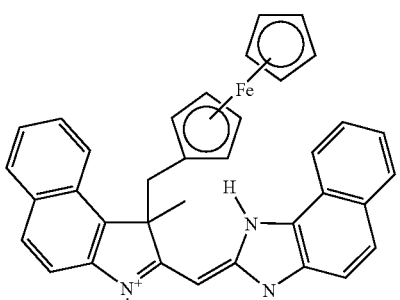
Compound No. 30

[Formula 18]
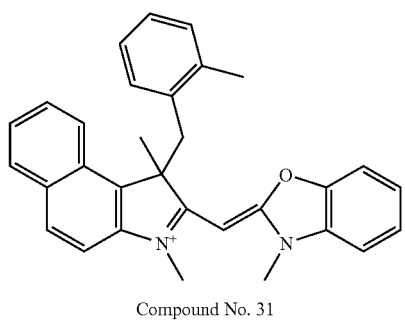
Compound No. 31
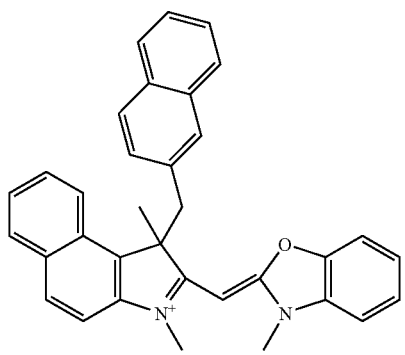
Compound No. 32
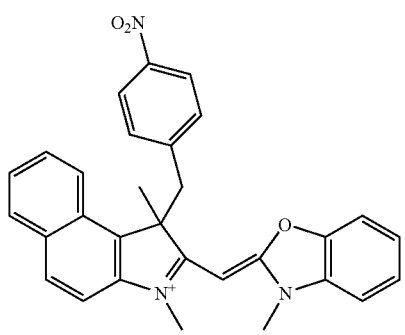
Compound No. 33
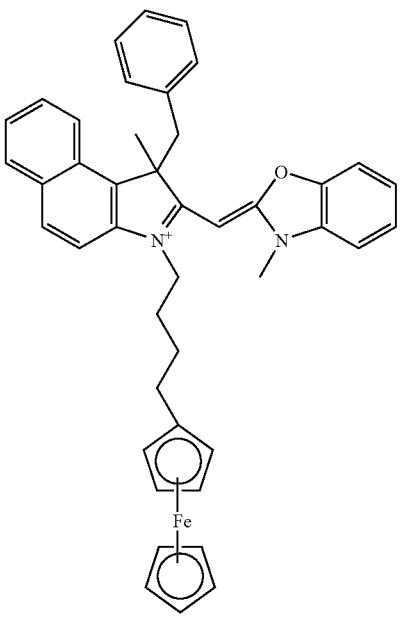
Compound No. 34
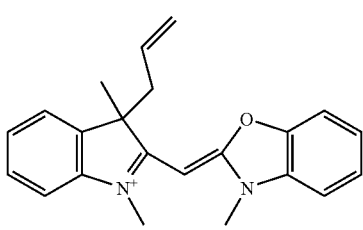
Compound No. 35
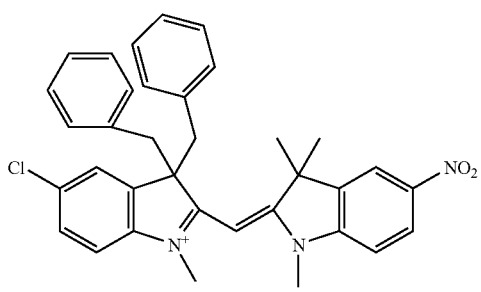
Compound No. 36
Compound No. 37

-continued
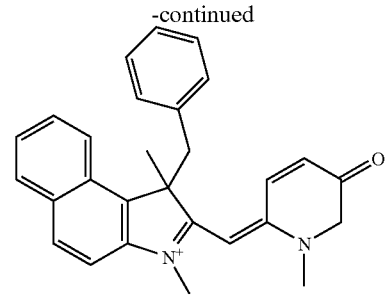
Compound No. 38
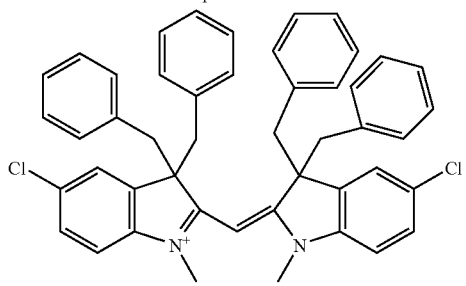
Compound No. 39
[Formula 19]
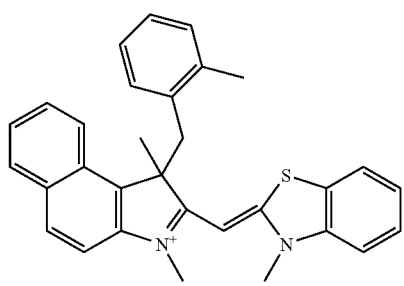
Compound No. 40
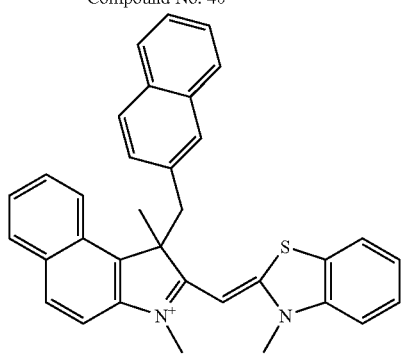
Compound No. 41
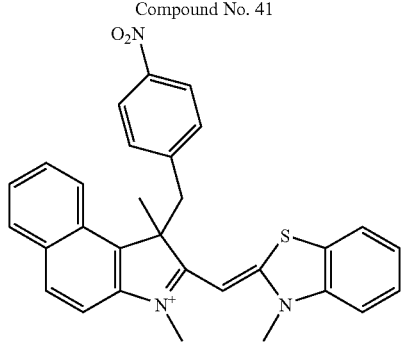
Compound No. 42
-continued
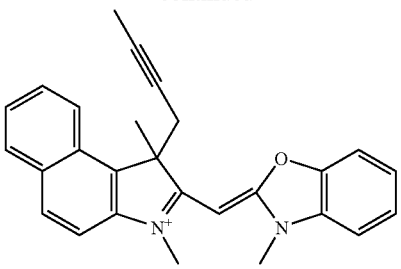
Compound No. 43
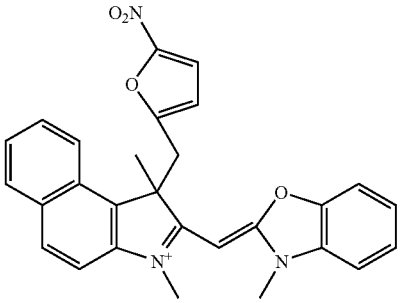
Compound No. 44
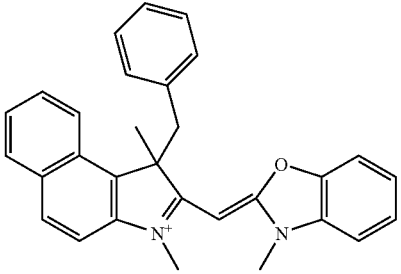
Compound No. 45
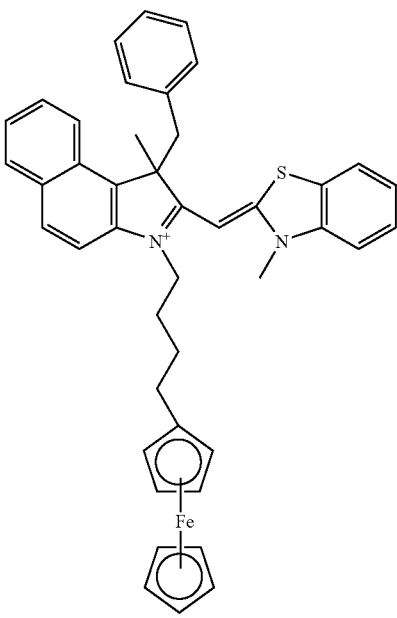
Compound No. 46

-continued

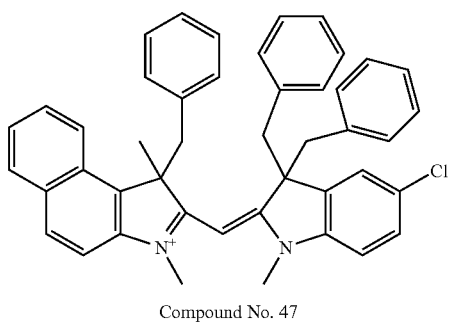

Compound No. 47

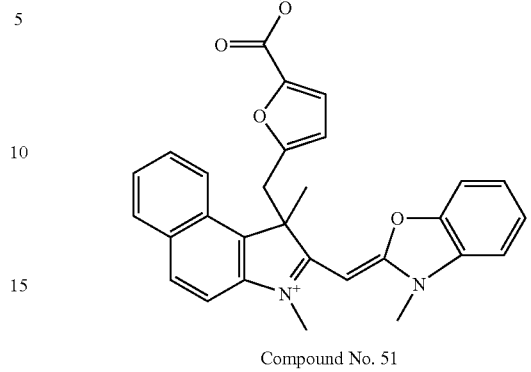

Compound No. 51

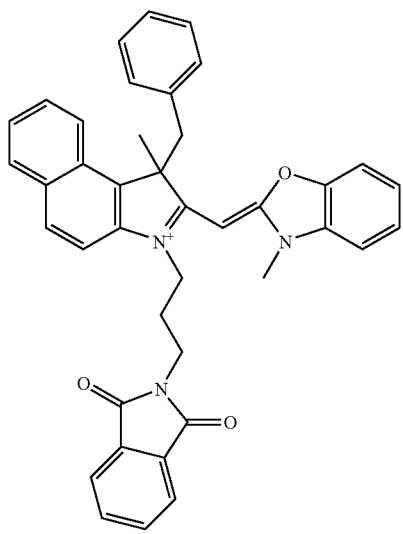

Compound No. 48

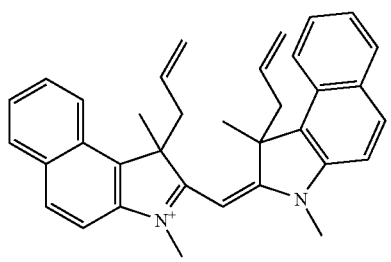

Compound No. 49

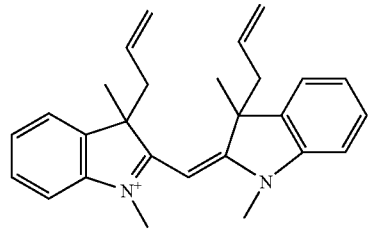

Compound No. 50

With the cyanine compound of the present invention represented by the general formula (I), there are cases where optical isomers such as enantiomers, diastereomers, or a racemic mixture are present, having, as the chiral center, the chiral atom to which groups represented by $R^7$ and $R^{12}$ are bonded. In such a case, any optical isomer among these may be isolated and used as such or may be used as a mixture thereof.

In addition, the same can be mentioned of the cyanine compound of the present invention represented by the general formula (VI).

The cyanine compound of the present invention, represented by the general formulae (I) and (VI), is not restricted by its manufacturing method and can be obtained by a method using publicly known reactions. For example, it can be prepared by oximating an indolenine quaternary salt according to the reaction formula shown in the following [Formula 20], and, the oximated product of the indolenine quaternary salt obtained according to the following [Formula 20] is reacted with an indolenine quaternary salt according to the reaction formula shown in [Formula 21], followed by, according to necessity, an anion exchange reaction. Alternatively, it can be synthesized by reacting the indolenine quaternary salt obtained according to the [Formula 20], with an indolenine quaternary salt having 2-methylthio group, according to the reaction formula shown in [Formula 22], followed by, according to necessity, an anion exchange reaction. Also, it may be prepared by a method described in Dyes and Pigments, Vol. 37, 1998, 205-211 or Liebigs Ann. Chem., 1981, 107-121. In addition, the indolenine quaternary salt can be prepared by a conventional method:

[Formula 20]

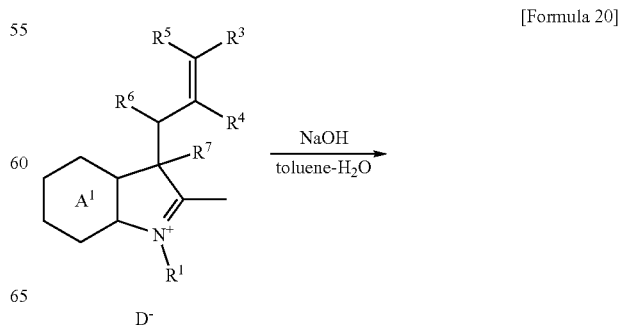

-continued

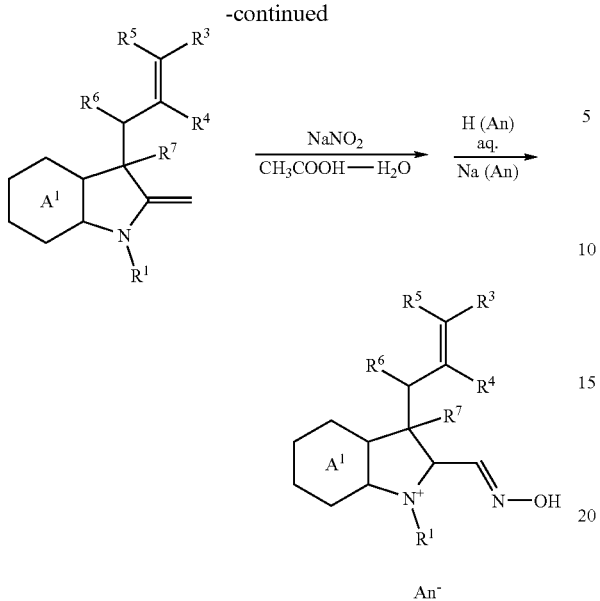

wherein, $A^1$, $R^1$, $R^3$, $R^4$, $R^5$, $R^6$, $R^7$, and An are the same as in the general formula (I); D represents an anion:

[Formula 21]

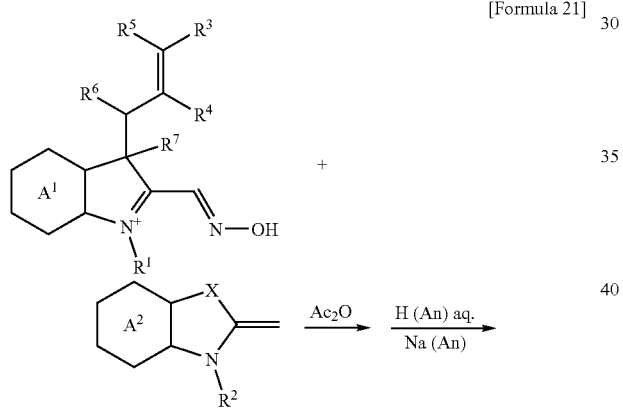

wherein, $A^1$, $A^2$, $R^1$, $R^2$, $R^3$, $R^4$, $R^5$, $R^6$, $R^7$, X, and An are the same as in the general formula (I):

[Formula 22]

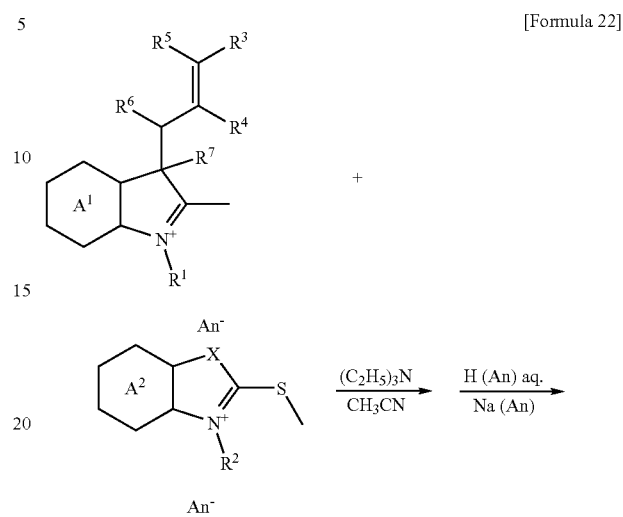

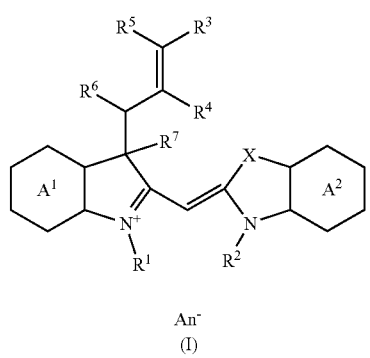

wherein, $A^1$, $A^2$, $R^1$, $R^2$, $R^3$, $R^4$, $R^5$, $R^6$, $R^7$, X, and An are the same as in the general formula (I).

In the following, the optical recording material of the present invention and optical recording medium comprising the optical recording material will be described.

The optical recording material of the present invention contains at least one kind of the cyanine compound of the present invention represented by the general formula (I) or (VI).

Further, the optical recording medium of the present invention is obtained by forming an optical recording layer comprising the optical recording material on a substrate and, thus, the optical recording material can be applied to various optical recording media depending on the light absorption characteristics of the cyanine compound contained in the material. Among the optical recording materials of the present invention, especially suitable for optical discs for short-wavelength laser of wavelength between 380 and 420 nm are those having a optical absorption characteristic dissolved in a solvent, the maximum absorption wavelength, λmax, in a range of 350 to 500 nm. Also, with regard to the absorption intensity, ε at λmax is preferably $1.0 \times 10^4$ or larger because when it is smaller than $1.0 \times 10^4$, there is a possibility that the recording sensitivity drops. Measurement of λmax and ε of the cyanine compound of the present invention, represented by the general formula (I) or (IV), can be made in a solution, according to the conventional method by selecting the concentration of the sample solution, kind of the solvent used for measurement, and the like.

There is no restriction on the method for forming the optical recording layer of the optical recording medium, using the optical recording material of the present invention which comprises the cyanine compound of the present invention, represented by the general formula (I) or (VI). Generally, the cyanine compound of the present invention and, if necessary, various compounds described later are dissolved in an organic solvent to obtain the optical recording material as a solution, the organic solvent including lower alcohols such as methanol, ethanol, and the like; ether alcohols such as methyl cellosolve, ethyl cellosolve, butyl cellosolve, butyl diglycol, and the like; ketones such as acetone, methyl ethyl ketone, methyl isobutyl ketone, cyclohexanone, diacetone alcohol, and the like; esters such as ethyl acetate, butyl acetate, methoxyethyl acetate, and the like; acrylic acid esters such as ethyl acrylate, butyl acrylate, and the like; fluorinated alcohols such as 2,2,3,3-tetrafluoropropanol; haydrocarbons such as benzene, toluene, xylene, and the like; chlorinated hydrocarbons such as methylene dichloride, dichloroethane, chloroform, and the like. The optical recording material solution is coated on the substrate by a wet coating method including spin coating, spraying, dipping, and the like. Methods such as vapor deposition, sputtering, and the like may also be used. When using the organic solvent, its amount used is preferably such that the content of the cyanine compound becomes 0.1 to 10% by mass of the optical recording material of the present invention.

The optical recording layer is formed as a thin film and its suitable thickness is usually 0.001 to 10 μm, preferably 0.01 to 5 μm.

Further, in the optical recording material of the present invention, the content of the cyanine compound of the present invention represented by the general formula (I) or (VI) is each preferably 10 to 100% by mass of the solid content of the optical recording material of the present invention. The optical recording layer is preferably formed in a manner such that the optical recording layer contains the cyanine compound of the present invention, represented by the general formula (I) or (VI), in an amount of 50 to 100% by mass. To form an optical recording layer of such a cyanine compound content, the optical recording material of the present invention more preferably contains the cyanine compound of the present invention, represented by the general formula (I) or (VI), in an amount of 50 to 100% by mass based on the solid content contained in the optical recording material of the invention.

The solid content of the optical recording material of the present invention refers to the components left after removing the components other than the solid content, namely, the solvent and the like, from the optical recording material. The solid content of the optical recording material is preferably 0.01 to 100% by mass, preferably 0.1 to 10% by mass.

In addition to the cyanine compound of the present invention, the optical recording material of the present invention may contain, according to necessity, a compound usually used for an optical recording layer such as azo compounds, phthalocyanines, oxonols, squarylium compounds, indoles, styryl compounds, porphyns, azlenium compounds, chroconicmethines, pyrilium compounds, thiopyrilium compounds, triarylmethanes, diphenylmethanes, tetrahydrocholines, indophenols, anthraquinones, naphthoquinones, xanthene compounds, thiazines, acridines, oxadines, spiropyrans, fluorenes, rhodamines, and the like; a resin such as polyethylene, polyester, polystyrene, polycarbonate and the like; a surfactant; an antistatic agent; a lubricating agent; a fire retardant; a radical trapping agent such as hindered amines; a pit formation accelerator such as a ferrocene derivative; a dispersant; an antioxidant; a crosslinking agent; a weatherability-providing agent, and the like. Further, the optical recording material of the present invention may contain, as a quencher of singlet oxygen and the like, an aromatic nitroso compound, an aminium compound, an iminium compound, a bisiminium compound, a transition metal chelate compound, and the like. In the optical recording material of the present invention, these various compounds are used in an amount of 0 to 50% by mass based on the solid content of the optical recording material of the present invention.

There is no particular restriction on the material used as the substrate on which such an optical recording layer is formed, provided that it is essentially transparent to the writing (recording) light and reading (reproducing) light, examples including resins such as polymethyl methacrylate, polyethylene terephthalate, polycarbonate, and the like; glass and the like. Further, its shape is optionally selected corresponding to the application, from a tape, drum, belt, disc, and the like.

Further, there may be formed on the optical recording layer a reflection film by vapor deposition or sputtering using gold, silver, aluminum, copper, and the like. A protection layer may also be formed using an acrylic resin, ultraviolet light-curable resin, or the like.

The optical recording material of the present invention is suitable for an optical recording medium, which is recorded and reproduced by use of a semiconductor laser, especially for publicly known single-, double-, or multi-layer discs such as CD-R, DVD±R, HD-DVD-R, BD-R, and the like, each of a high-speed recording type.

As described above, the cyanine compound of the present invention is used suitably as an optical recording material. In addition, it may also be used as a light absorbing agent added to optical filters for image display units; a photosensitive material for dye-sensitized solar cells, electrochemical photocells, nonlinear optical instruments, electrochromic displays, holograms, organic semiconductors, organic EL, silver halide photography; a photo-sensitizer; a colorant for printing ink, inkjet, electrophotography clor toner, color filters, reflection display, cosmetics, plastics, and the like; a dyeing agent for proteins; a luminescent dye for identification of materials, and the like.

EXAMPLES

Hereafter, the present invention will be described in more detail in terms of Manufacturing Examples and Examples. However, the present invention will not be limited in any way by the following Examples and the like.

The following Manufacturing Examples 1 to 12 show examples of manufacture of the cyanine compounds of the present invention. Further, the following Examples 1 to 12 show examples of optical recording material and optical recording medium of the present invention using the cyanine compound of the present invention obtained in Manufacturing Examples 1 to 12. Comparative Example 1 shows an example of an optical recording material and an optical recording medium, which was prepared using a cyanine compound of a structure different from the cyanine compound of the present invention. Also, in the following Evaluation Example 1, thermal decomposition behavior was evaluated by measuring the melting and decomposition points of the cyanine compound of the present invention obtained in Manufacturing Examples 1 to 12, as well as the cyanine compound used in Comparative Example having a different structure from the cyanine compound of the present invention. Further, in the following Evaluation Example 2 was evaluated light resistance of the cyanine compounds of the present invention obtained in Manufacturing Examples 2 and 4 to 6, and the cyanine compound No. 39 of the present invention. In the following Evaluation Example 3 was evaluated heat resistance of the cyanine compound of the present invention obtained in Manufacturing Example 2 and the cyanine compound No. 39 of the present invention.

Manufacturing Examples 1 to 3, 5, and 8 to 12

Manufacture of Cyanine Compounds

Using Synthetic Method 1 or 2 described below, synthesized were tetrafluoroborate salts of compound Nos. 1 to 3, compound No. 41, and compound No. 51; an iodide salt of compound No. 43; a bromide salt of compound No. 40; a perchlorate salt of compound No. 42; and a hexafluorophosphate salt of compound No. 34. The compounds obtained were identified by IR and $^1$H-NMR analyses. The analytical results are shown in [Table 2] and [Table 3]. Also, in [Table 1], yields of the compounds obtained and results of measurement of the characteristic values [optical absorption characteristics (λmax and ε at λmax) dissolved in a solution] are shown.
(Synthetic Method 1) Synthesis of Compound Nos. 2, 35, and 36
<Step 1> Manufacture of Oxime Derivatives of Indolenine Quaternary Salts To a reaction vessel were charged 0.10 mol of an indolenine quaternary salt and 76 g of toluene, and to this was dropwise added 80 g of 10% aq. sodium hydroxide at 0° C. over 15 min., followed by stirring at room temperature for 3 hrs. The organic layer was extracted, washed with water, dried over anhydrous sodium sulfate, and the solvent was removed by evaporation. Then, after addition of 25 g of acetic acid, a solution of 60 mmol of sodium nitrite dissolved in 50 g of water was dropwise added at 0° C. over 15 min., followed by stirring for 1 hr at room temperature. To this was added a solution of 20 g of 48% aq. tetrafluoroboric acid and 0.23 mol of sodium tetrafluoroborate dissolved in 50 g of water, and the mixture was stirred overnight. The precipitated solid was collected by filtration, washed with water, and recrystallized from a mixed solvent of ethanol:ethyl acetate:toluene=3:2:5 to obtain a respective, desired oxime derivative of the indolenine quaternary salt.
<Step 2> Manufacture of a Cyanine Compound To a reaction vessel were charged 10 mmol of the oxime derivative of the indolenine quaternary salt, 10 mmol of N-alkyl-2-methyleneindolium compound, and 20 g of acetic anhydride, and the mixture was stirred at 90° C. for 2 hrs. After anions were exchanged by a conventional method, the organic layer was extracted by addition of 40 g of chloroform, washed with water, dried over anhydrous sodium sulfate, and the solvent was removed by distillation. The residue was purified by column chromatography (silica gel, chloroform:acetone=10:1), recrystallized from 20 g of methanol, and dried under vacuum to obtain a respective, desired cyanine compound.
(Synthetic Method 2) Synthesis of Compound Nos. 1, 3, 34, 40 to 43, and 51

To a reaction vessel were charged 10 mmol of an indolenine quaternary salt, 10 mmol of N-alkyl-2-methylthioindolium compound, 0.02 mmol of triethylamine, and 16 g of acetonitrile, and the mixture was stirred at room temperature for 4 hrs. and at 50° C. for 3 hrs. After anions were exchanged by a conventional method, the precipitated solid was collected by filtration, washed with chloroform and water, and dried under vacuum to obtain a respective, desired cyanine compound.

Manufacturing Example 4

Manufacture of a Quencher Anion (C) Salt of Cyanine Compound No. 2

To a reaction vessel were charged 0.69 mmol of tetrafluoroborate salt of cyanine compound No. 2, 0.69 mmol of a triethylamine salt of the anion represented by the chemical formula [C], and 3.6 g of pyridine, and the mixture was stirred at 60° C. for 2 hrs. and, after addition of 8 g of methanol, was allowed to cool to room temperature. The precipitated solid was collected by filtration and dried under vacuum to obtain the desired quencher anion (C) salt of compound No. 2. The compound obtained was identified by IR and $^1$H-NMR analyses. The analytical results are shown in [Table 2] and [Table 3]. Also, in [Table 1], the yield of the compound synthesized and results of measurement of the characteristic values [optical absorption characteristics (λmax and ε at λmax) dissolved in a solution] are shown.

Manufacturing Examples 6 and 7

Manufacture of Quencher Anion (D) Salts of Cyanine Compound Nos. 35 and No. 36

Except that triethylamine salt of an anion represented by the chemical formula (D) was used instead of the triethylamine salt of anion represented by the chemical formula (C), the reaction was carried out in a similar manner as in Manufacturing Example 4 to obtain the respective, desired quencher anion (D) salts of compound Nos. 35 and 36. The compounds obtained were identified by IR and $^1$H-NMR analyses. The analytical data are shown in [Table 2] and [Table 3]. Also, in [Table 1], yields of the compounds synthesized and results of measurement of the characteristic values [optical absorption characteristics (λmax and ε at λmax) in solution state] are shown.

TABLE 1

| | Cyanine compound | Yield (%) | λmax | ε ($\times 10^4$) |
|---|---|---|---|---|
| Manufacturing Example 1 | Tetrafluoroborate salt of compound No. 1 | 36 | 460.0 | 4.37 |
| Manufacturing Example 2 | Tetrafluoroborate salt of compound No. 2 | 8.3 | 475.5 | 3.86 |
| Manufacturing Example 3 | Tetrafluoroborate salt of compound No. 3 | 60 | 457.5 | 4.74 |
| Manufacturing Example 4 | Quencher anion (C) salt of compound No. 2 | 78 | 504.0 | 8.09 |
| Manufacturing Example 5 | Hexafluorophosphate salt of compound No. 34 | 19 | 424.0 | 4.80 |
| Manufacturing Example 6 | Quencher anion (D) salt of compound No. 35 | 60 | 451.0 | 7.31 |
| Manufacturing Example 7 | Quencher anion (D) salt of compound No. 36 | 88 | 476.0 | 8.13 |
| Manufacturing Example 8 | Bromide salt of compound No. 40 | 56 | 420.5 | 4.47 |
| Manufacturing Example 9 | Tetrafluoroborate salt of compound No. 41 | 59 | 420.5 | 4.35 |
| Manufacturing Example 10 | Perchlorate salt of compound No. 42 | 39 | 420.5 | 4.52 |
| Manufacturing Example 11 | Iodide salt of compound No. 43 | 59 | 418.5 | 4.44 |
| Manufacturing Example 12 | Tetrafluoroborate salt of compound No. 51 | 15 | 420.0 | 4.34 |

TABLE 2

| | Cyanine compound | IR spectrum (cm$^{-1}$) |
|---|---|---|
| Manufacturing Example 1 | Tetrafluoroborate salt of compound No. 1 | 3028, 1598, 1560, 1520, 1470, 1368, 1310, 1281, 1166, 1144, 1053 |
| Manufacturing Example 2 | Tetrafluoroborate salt of compound No. 2 | 3447, 1590, 1559, 1521, 1458, 1388, 1313, 1144, 1057 |
| Manufacturing Example 3 | Tetrafluoroborate salt of compound No. 3 | 3471, 1596, 1542, 1518, 1475, 1369, 1354, 1321, 1307, 1169, 1144, 1062 |
| Manufacturing Example 4 | Quencher anion (C) salt of compound No. 2 | 3437, 1609, 1577, 1557, 1526, 1457, 1388, 1324, 1261, 1166, 1141, 1123, 1071 |
| Manufacturing Example 5 | Hexafluorophosphate salt of compound No. 34 | 3424, 2945, 1590, 1568, 1519, 1482, 1441, 1401, 1342, 1298, 1268 |
| Manufacturing Example 6 | Quencher anion (D) salt of compound No. 35 | 2963, 2218, 1655, 1568, 1513, 1472, 1385, 1323, 1296 |
| Manufacturing Example 7 | Quencher anion (D) salt of compound No. 36 | 2958, 2219, 1654, 1638, 1567, 1514, 1396, 1383, 1339, 1324, 1299 |
| Manufacturing Example 8 | Bromide salt of compound No. 40 | 3435, 2998, 1612, 1595, 1573, 1538, 1521, 1483, 1396, 1330, 1302, 1270 |
| Manufacturing Example 9 | Tetrafluoroborate salt of compound No. 41 | 3060, 1590, 1567, 1519, 1482, 1469, 1396, 1325, 1299, 1255, 1239, 1200 |
| Manufacturing Example 10 | Perchlorate salt of compound No. 42 | 3078, 2946, 1593, 1572, 1521, 1481, 1397, 1343, 1328, 1270, 1228, 1199 |
| Manufacturing Example 11 | Iodide salt of compound No. 43 | 3452, 3014, 1591, 1567, 1520, 1479, 1434, 1402, 1357, 1326, 1268, 1243, 1200 |
| Manufacturing Example 12 | Tetrafluoroborate salt of compound No. 51 | 3529, 3420, 2986, 1696, 1594, 1570, 1520, 1483, 1442, 1399, 1358, 1327, 1303 |

TABLE 3

| | Cyanine compound | $^1$H-NMR (solvent DMSO-d6) (ppm) |
|---|---|---|
| Manufacturing Example 1 | Tetrafluoroborate salt of compound No. 1 | 8.46 (d, 1H), 8.14 (d, 1H), 8.06 (d, 1H), 8.00 (t, 2H), 7.72 (m, 2H), 7.56 (m. 2H), 7.45 (d, 1H), 6.94 (t, 1H), 6.82 (t, 2H), 6.45 (s, 1H), 6.44 (d, 2H), 4.12 (s, 3H), 3.90 (dd, 2H), 3.31 (s, 3H), 2.05 (s, 3H) |
| Manufacturing Example 2 | Tetrafluoroborate salt of compound No. 2 | 8.55 (d, 2H), 8.07 (d, 2H), 7.88 (d, 2H), 7.80 (t, 2H), 7.63 (t, 2H), 7.47 (d. 2H), 6.98 (m, 2H), 6.89 (m, 4H), 6.71 (s, 1H), 6.54 (d, 4H), 4.00 (dd, 4H), 2.74 (s, 6H), 2.08 (s, 6H), |
| Manufacturing Example 3 | Tetrafluoroborate salt of compound No. 3 | 8.27 (d, 1H), 8.08 (m, 3H), 7.95 (d, 1H), 7.70 (m, 3H), 7.54 (m, 2H), 6.27 (s. 1H), 4.78 (m 2H), 4.05 (s, 3H), 3.39 (dd, 2H), 1.90 (s, 3H) |
| Manufacturing Example 4 | Quencher anion (C) salt of compound No. 2 | 9.00 (s, 2H), 8.55 (d, 2H), 8.11 (d, 2H), 8.05 (t, 2H), 7.85 (d, 2H), 7.80 (t. 2H), 7.65 (t 2H), 7.60 (d, 2H), 7.46 (d, 2H), 6.97(t. 2H), 6.89 (t, 4H), 6.65 (s, 1H), 6.54 (d, 4H), 6.51 (d. 2H), 5.74 (s 2H), 3.99 (m, 4H), 3.29 (m, 8H), 2.73 (s, 6H), 2.07 (s, 6H), 1.03 (t, 12H) |
| Manufacturing Example 5 | Hexafluorophosphate salt of compound No. 34 | 8.45 (d, 1H), 8.08 (d, 1H), 8.01 (d, 1H), 7.94(t, 1H), 7.83(d, 1H), 7.74(t, 1H), 7.64-7.52 (m, 3H), 7.47 (d. 1H), 6.93 (t, 1H), 6.80 (t, 2H), 6.41 (d, 2H), 5.69 (s, 1H), 4.14-3.92 (m, 16H), 2.22 (t, 2H), 2.08 (s, 3H), 1.38-1.26 (m, 4H) |
| Manufacturing Example 6 | Quencher anion (D) salt of compound No. 35 | 9.02 (d, 2H), 7.97 (dd, 1H), 7.64 (d, 1H), 7.61 (d, 1H), 7.61 (d, 1H), 7.54-7.42 (m. 4H), 7.39-7.31 (m, 2H), 6.88 (d, 2H), 5.72 (s, 1H), 5.27-5.10 (m, 1H), 5.03 (dd, 1H), 4.91 (dd, 1H), 3.59-3.44 (m, 4H), 3.32 (s, 3H), 3.22 (s, 3H), 2.93-2.80 (m, 2H), 2.88 (s, 6H), 1.60 (s, 3H), 1.59 (s, 3H), 1.56 (s, 3H), 0.91 (tt, 4H), 0.75 (tq, 4H), 0.44 (t, 6H) |
| Manufacturing Example 7 | Quencher anion (D) salt of compound No. 36 | 9.02 (d, 2H), 8.58 (d, 1H), 8.35 (dd, 1H), 8.22 (d, 1H), 7.97 (dd, 2H), 7.52 (d, 1H), 7.51 (d, 1H), 7.13 (d, 1H), 7.11-6.98 (m 6H), 6.88 (d, 2H), 6.84-6.69 (br, 4H), 6.32 (s, 1H), 3.89-3.40 (br, 4H), 3.60-3.44 (m, 4H), 2.88 (s, 6H), 2.67 (s, 3H), 2.55 (s, 3H), 1.83-1.68 (br, 6H), 0.91 (tt, 4H), 0.75 (tq, 4H), 0.44 (t, 6H) |
| Manufacturing Example 8 | Bromide salt of compound No. 40 | 8.21 (d, 1H), 8.02 (d, 2H), 7.91 (d, 1H), 7.79 (d, 1H), 7.57-7.47 (m, 5H), 6.87 (t, 1H), 6.78-6.73 (m, 2H), 6.64 (d, 1H), 5.79 (s, 1H), 3.93 (m, 5H), 3.63 (s, 3H), 2.12 (s, 3H), 1.71 (s, 3H) |

TABLE 3-continued

| | Cyanine compound | ¹H-NMR (solvent DMSO-d6) (ppm) |
|---|---|---|
| Manufacturing Example 9 | Tetrafluoroborate salt of compound No. 41 | 8.52 (d, 1H), 8.06 (d, 1H), 7.93 (d, 2H), 7.85-7.78 (m, 2H), 7.62-7.56 (m, 4H), 7.37-7.27 (m, 5H), 6.54 (d, 1H), 5.76 (s, 1H), 4.39-4.01 (m, 5H), 3.42 (s, 3H), 2.19 (s, 3H) |
| Manufacturing Example 10 | Perchlorate salt of compound No. 42 | 8.46 (d, 1H), 8.08-7.44 (m, 1H), 6.75 (d, 2H), 5.76 (s, 1H), 4.35-4.00 (m, 5H), 3.49 (s, 3H), 2.19 (s, 3H) |
| Manufacturing Example 11 | Iodide salt of compound No. 43 | 8.22 (d, 1H), 8.11 (d, 1H), 8.07 (d, 1H), 7.87 (d, 1H), 7.97-7.74 (m, 2H), 7.66-7.49 (m, 4H), 5.79 (s, 1H), 3.95 (s, 3H), 3.81(s, 3H), 3.27 (s, 2H), 1.96 (s, 3H), 1.37 (s, 3H) |
| Manufacturing Example 12 | Tetrafluoroborate salt of compound No. 51 | 8.30 (d, 1H), 8.03 (m, 2H), 7.90 (d, 1H), 7.80 (d, 1H), 7.69-7.49 (m, 6H), 6.77 (d, 1H), 5.67 (s, 1H), 4.14-3.91 (m, 5H), 3.69 (s, 3H), 3.29 (s, 2H), 2.19 (s, 3H), 1.10 (t 3H) |

Examples 1 to 12

Preparation of Optical Recording Materials and Optical Recording Media

The cyanine compounds obtained in the Manufacturing Examples 1 to 12 were each dissolved in 2,2,3,3-tetrafluoropropanol in concentration of 1.0% by mass to obtain the optical recording materials of Examples 1 to 12, respectively as a 2,2,3,3-tetrafluoropropanol solution. The optical recording material was spin coated on a polycarbonate disc substrate of 12 cm diameter to form a 100 nm thick optical recording layer, the disc having been provided with a foundation layer (0.01 μm) by coating a titanium chelate compound (T-50: manufactured by Nippon Soda Co., Ltd.), followed by hydrolysis. Thus were obtained the optical recording media of Examples 1 to 12, respectively.

Comparative Example 1

Except that the following Comparative Compound No. 1 was used as the cyanine compound, the optical recording material of Comparative Example 1 was obtained as a 2,2,3,3-tetrafluoropropanol solution, in a similar manner as in Examples 1 to 12, by dissolving the compound in 2,2,3,3-tetrafluoropropanol. The optical recording material was spin coated on a polycarbonate disc substrate of 12 cm diameter, with a foundation layer (0.01 μm) provided thereon by coating a titanium chelate compound (T-50: manufactured by Nippon Soda Co., Ltd.), followed by hydrolysis. However, immediately after coating, crystals precipitated and, thus, the optical recording medium could not be obtained.

[Formula 23]

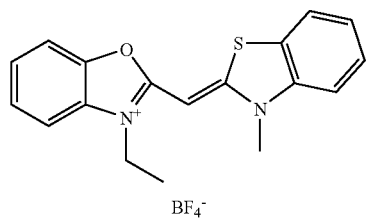

Comparative compound No. 1

Evaluation Example 1

Melting and decomposition points were measured in order to evaluate the thermal decomposition behavior of the cyanine compounds of the present invention, obtained in Manufacturing Examples 1 to 12, as well as the cyanine compound used in Comparative Example with a structure different from those of the present invention. The results are shown in [Table 4].

In [Table 4], the decomposition point refers to the temperature in the differential thermal analysis performed at a heating rate of 110° C./min., whereat the mass of a sample begins to decrease.

TABLE 4

| | Cyanine compound | Melting point (° C.) | Decomposition point (° C.) |
|---|---|---|---|
| Evaluation Example 1-1 | Tetrafluoroborate salt of compound No. 1 | 216 | 264 |
| Evaluation Example 1-2 | Tetrafluoroborate salt of compound No. 2 | — | 246 |
| Evaluation Example 1-3 | Tetrafluoroborate salt of compound No. 3 | 229 | 277 |
| Evaluation Example 1-4 | Quencher anion (C) salt of compound No. 2 | — | 232 |
| Evaluation Example 1-5 | Hexafluorophosphate salt of compound No. 34 | — | 248 |
| Evaluation Example 1-6 | Quencher anion (D) salt of compound No. 35 | 229 | 243 |
| Evaluation Example 1-7 | Quencher anion (D) salt of compound No. 36 | 249 | 254 |
| Evaluation Example 1-8 | Bromide salt of compound No. 40 | — | 264 |
| Evaluation Example 1-9 | Tetrafluoroborate salt of compound No. 41 | — | 238 |
| Evaluation Example 1-10 | Perchlorate salt of compound No. 42 | — | 239 |
| Evaluation Example 1-11 | Iodide salt of compound No. 43 | — | 249 |
| Evaluation Example 1-12 | Tetrafluoroborate salt of compound No. 51 | — | 205 |
| Comparative Evaluation Example 1-1 | Comparative compound No. 1 | — | 309 |

The results listed in [Table 4] show that the cyanine compounds of the present invention decompose at temperatures below 300° C., lower temperatures relative to the cyanine compound of Comparative Example. It is generally known that an optical recording medium, comprised of an optical recording material containing a compound which decomposes below 300° C., shows ideal recording characteristics. Thus, the cyanine compounds of the present invention were confirmed to show ideal thermal decomposition behavior for an optical recording material.

Evaluation Examples 2 and 3

Light resistance of tetrafluoroborate salts of the compounds obtained in Manufacturing Examples 2 and 4 to 6, and Compound No. 39, as well as heat resistance of tetrafluoroborate salts of the compound obtained in Manufacturing Example 2 and Compound No. 39 were measured. First, the compounds of the present invention were dissolved in 2,2,3,3-tetrafluoropropanol in concentrations of 1% by mass in order to prepare 2,2,3,3-tetrafluoropropanol solutions and the solutions obtained were coated on 20×20 mm polycarbonate plates by a spin coating method at 2000 rpm for 60 seconds to prepare the respective test pieces.

<Evaluation of Light Resistance>

With each of the test pieces, absorbance at λmax in the UV absorption spectrum was measured and, then, the test pieces were irradiated with a 55,000 lux light for 96 hrs., whereupon absorbance at λmax in the UV absorption spectrum was measured again. The light stability was evaluated from a ratio of the absorbance after irradiation relative to the absorbance before irradiation, the latter being regarded as 100. The results are shown in [Table 5].

<Evaluation of Heat Stability>

With each of the test pieces, transmittance at λmax in UV absorption spectrum was measured and the test piece was stored in a thermostatic chamber at 120° C. for 134 hrs, whereupon transmittance at λmax in UV absorption spectrum was measured again, The heat stability was evaluated from a ratio of the transmittance after storing relative to the transmittance before storing, the latter being regarded as 100. The results are shown in [Table 6].

TABLE 5

|  | Cyanine compound | Light stability (%) |
|---|---|---|
| Evaluation Example 2-1 | Tetrafluoroborate salt of Compound No. 2 | 0 |
| Evaluation Example 2-2 | Quencher anion (C) salt of Compound No. 2 | 88.9 |
| Evaluation Example 2-3 | Hexafluorophosphate salt of Compound No. 34 | 87.4 |
| Evaluation Example 2-4 | Quencher anion (D) salt of Compound No. 35 | 98.2 |
| Evaluation Example 2-5 | Tetrafluoroborate salt of Compound No. 39 | 0 |

TABLE 6

|  | Cyanine compound | Heat stability (%) |
|---|---|---|
| Evaluation Example 3-1 | Tetrafluoroborate salt of Compound No. 2 | 64.6 |
| Evaluation Example 3-2 | Tetrafluoroborate salt of Compound No. 39 | 26.7 |

Among the cyanine compounds of the present invention, the quencher anion (C) salt of Compound No. 2, and the quencher anion (D) salt of Compound No. 35, both having a metal complex anion, and a hexafluorophosphate salt of Compound No. 34, having a substituent containing a metallocene structure, have high residual ratios of absorbance after 96 hrs. of light irradiation and thus these were confirmed to be suitable as compounds used in optical recording media. Further, tetrafluoroborate salts of Compounds No. 2 and No. 39, which contain neither metal complex anions nor metallocene structure, were confirmed to possess enough heat stability to withstand deterioration by reproducing light, when used for optical recording media.

INDUSTRIAL APPLICABILITY

The present invention provides a cyanine compound which has a light absorption characteristic suitable for forming an optical recording layer of an optical recording medium for short-wavelength recording light, and also provides an optical recording material comprising the compound. Further, the optical recording medium, having an optical recording layer formed using the optical recording material of the present invention, has a characteristic of excellent recording properties.

The invention claimed is:

1. A cyanine compound represented by the following general formula (I):

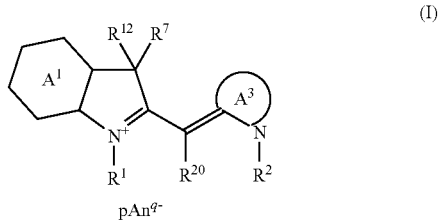

wherein:
ring $A^1$ represents benzene or naphthalene ring;
ring $A^3$ represents 5-membered or 6-membered ring, where the 5-membered or 6-membered ring may be condensed with other rings or may be substituted;
$R^1$ and $R^2$ each independently represent a hydrogen atom, an alkyl group having 1 to 8 carbon atoms, an aryl group having 6 to 20 carbon atoms, an arylalkyl group having 7 to 20 carbon atoms, a substituent represented by the following general formulas (II), (II'), or (III); and at least one of $R^1$ or $R^2$ is a substituent represented by the general formula (III);
$R^7$ represents an alkyl group having 1 to 8 carbon atoms, an aryl group having 6 to 20 carbon atoms, an arylalkyl group having 7 to 20 carbon atoms, or a substituent represented by general formula (II) or (II');
$R^{12}$ represents a substituent represented by general formula (II) or (II');
$R^{20}$ represents a hydrogen atom, a hydroxyl group, a halogen atom, a nitro group, a cyano group, an alkyl group having 1 to 8 carbon atoms, an aryl group having 6 to 20 carbon atoms, an arylalkyl group having 7 to 20 carbon atoms, a heterocyclic group having 2 to 20 carbon atoms, or an amino group, wherein a methylene group of said alkyl group having 1 to 8 carbon atoms may be replaced by —O—, —S—, —CO—, —COO—, —SO$_2$—, —NH—, —CONH—, —N=CH—, —C≡C—, or —CH=CH—; and
Anq- represents a q-valent anion, wherein q represents 1 or 2 and p represents a coefficient to keep the charge of the cyanine compound neutral;

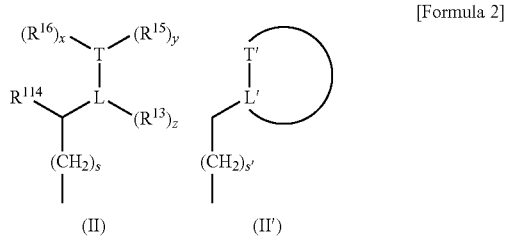

[Formula 2]

wherein, in general formula (II):
  the bond between L and T is a double, conjugated double, or triple bond;
  L represents a carbon atom;
  T represents a carbon, oxygen, sulfur, or nitrogen atom;
  x, y, and z represent 0 or 1;
  s represents a number from 0 to 4;
  $R^{13}$ represents a hydrogen atom, a halogen atom, an alkyl group having 1 to 4 carbon atoms which may be substituted with a halogen atom, or an alkoxy group having 1 to 4 carbon atoms which may be substituted with a halogen atom; and
  $R^{14}$, $R^{15}$, and $R^{16}$ each independently represent a hydrogen atom, a halogen atom, an alkyl group having 1 to 4 carbon atoms which may be substituted with a halogen atom, or an aryl group having 6 to 12 carbon atoms, where $R^{14}$ and $R^{16}$ may be linked to form a ring structure;
and wherein, in general formula (II'):
  the bond between L' and T' is a double or conjugated double bond;
  L' represents a carbon atom;
  T' represents a carbon, oxygen, or nitrogen atom;
  s' represents a number from 0 to 4;
  the ring containing L' and T' represents a 5-membered or 6-membered ring which may contain a hetero atom, or a naphthalene, quinoline, isoquinoline, anthracene, or anthraquinone ring; and
  the rings containing L' and T' may be substituted with a halogen atom, or a nitro, cyano, alkyl, or alkoxy group;

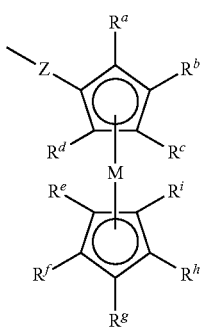

(III)

wherein, in general formula III:
  $R^a$ to $R^i$ each independently represent a hydrogen atom, a hydroxy group, or an alkyl group having 1 to 4 carbon atoms, and a methylene group of said alkyl group having 1 to 4 carbon atoms may be replaced by —O— or —CO—;
  Z represents a direct bond or an alkylene group having 1 to 8 carbon atoms which may be substituted, and a methylene group of said alkylene group having 1 to 8 carbon atoms may be replaced by —O—, —S—, —CO—, —COO—, —OCO—, $SO_2$—, —NH—, —CONH—, —NHCO—, —N=CH—, or —CH=CH—; and
  M represents a metal atom.

2. The cyanine compound according to claim 1, wherein the cyanine compound is represented by general formula (IV):

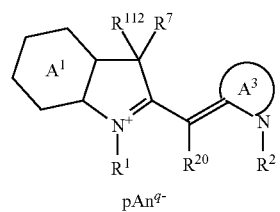

(IV)

wherein:
  $R_{112}$ represents a substituent represented by general formula (II''); and
  the rings $A^1$ and $A^3$, $R^1$, $R^2$, $R^7$, $R^{20}$, $An^{q-}$, q, and p are the same as in the general formula (I):

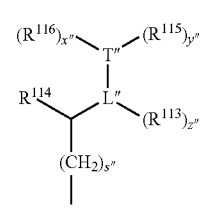

(II'')

wherein
  the bond between L'' and T'' is a double or triple bond;
  L'' represents a carbon atom;
  T'' represents a carbon, oxygen, sulfur, or nitrogen atom;
  x'', y'', and z'' represent 0 or 1;
  s'' represents a number from 0 to 4;
  $R^{113}$ represents a hydrogen atom, a halogen atom, an alkyl group having 1 to 4 carbon atoms which may be substituted with a halogen atom, or an alkoxy group having 1 to 4 carbon atoms which may be substituted with a halogen atom; and
  $R^{114}$, $R^{115}$, and $R^{116}$ each independently represent a hydrogen atom, a halogen atom, an alkyl group having 1 to 4 carbon atoms which may be substituted with a halogen atom, or an aryl group having 6 to 12 carbon atoms.

3. The cyanine compound according to claim 1, wherein the cyanine compound is represented by general formula (V):

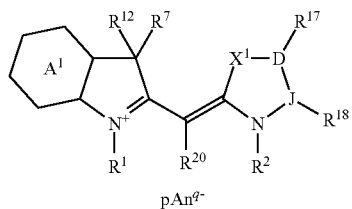

(V)

wherein:
  $X^1$ is an oxygen, sulfur, or selenium atom, or —NH—, or —NR—;
  the bond between D and J is a single, double, or conjugated double bond;
  D and J are carbon atoms;
  $R^{17}$, $R^{18}$, and R each independently represent a hydrogen atom, an alkyl group having 1 to 8 carbon atoms, an aryl group having 6 to 20 carbon atoms, an arylalkyl group having 7 to 20 carbon atoms, or a substituent represented by the general formula (II) or (II'); and
  the rings $A^1$ and $R^1$, $R^2$, $R^7$, $R^{12}$, $R^{20}$, $An^{q-}$, q, and p are the same as in the general formula (I):

4. The cyanine compound according to claim 1, wherein the ring $A^1$ in the general formula (I) is a naphthalene ring.

5. The cyanine compound according to claim 1, wherein $An^{q-}$ in the general formula (I) is a q-valent anion not comprising an azo bond.

6. An optical recording material comprising at least one kind of cyanine compound according to claim 1.

7. An optical recording medium comprising an optical recording layer formed by an optical recording material according to claim 6 on a substrate.

8. An optical recording material comprising at least one cyanine compound according to claim 2.

9. An optical recording material comprising at least one kind of cyanine compound according to claim 3.

10. An optical recording material comprising at least one kind of cyanine compound according to claim 4.

11. An optical recording material comprising at least one cyanine compound according to claim 5.

12. A cyanine compound selected from the group consisting of:

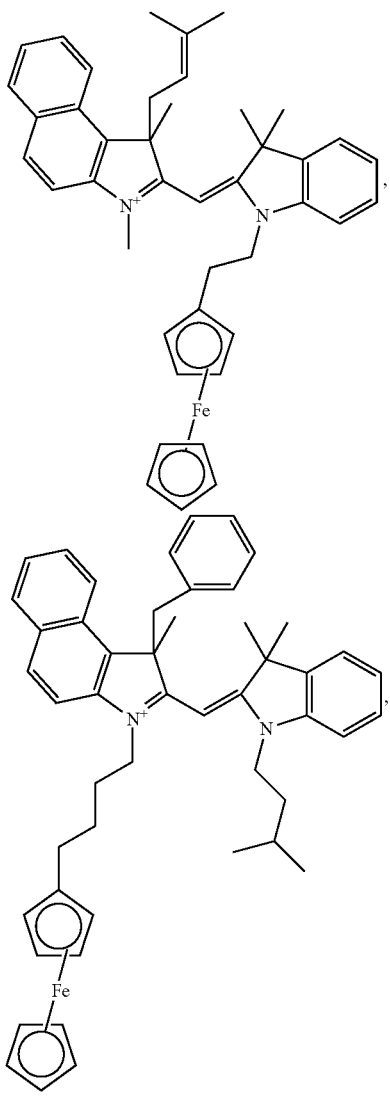
,

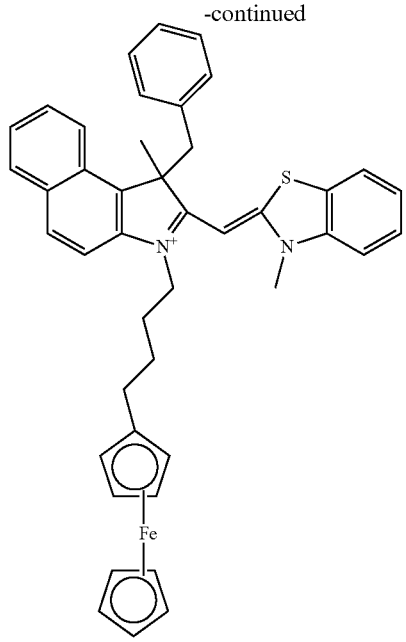
and

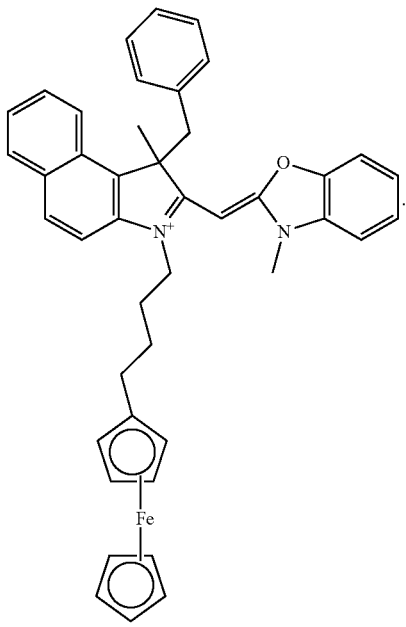
.

13. An optical recording material comprising at least one cyanine compound according to claim 12.

* * * * *